US007718376B2

(12) United States Patent
Simmons

(10) Patent No.: US 7,718,376 B2
(45) Date of Patent: May 18, 2010

(54) IDENTIFICATION AND ISOLATION OF SOMATIC STEM CELLS AND USES THEREOF

(75) Inventor: Paul John Simmons, Kew (AU)

(73) Assignees: Peter MacCallum Cancer Institute, East Melbourne, Victoria (AU); Medvet Science Pty Ltd., Stepney, South (AU)

( * ) Notice: Subject to any disclaimer, the term of this patent is extended or adjusted under 35 U.S.C. 154(b) by 756 days.

(21) Appl. No.: 10/486,845

(22) PCT Filed: Aug. 15, 2002

(86) PCT No.: PCT/AU02/01101

§ 371 (c)(1),
(2), (4) Date: Jul. 19, 2004

(87) PCT Pub. No.: WO03/016916

PCT Pub. Date: Feb. 27, 2003

(65) Prior Publication Data

US 2006/0088890 A1 Apr. 27, 2006

(30) Foreign Application Priority Data

Aug. 15, 2001 (AU) .................................. PR7036

(51) Int. Cl.
G01N 33/53 (2006.01)
G01N 33/532 (2006.01)
G01N 33/68 (2006.01)
C12N 5/00 (2006.01)
C07K 14/435 (2006.01)
C07K 7/00 (2006.01)

(52) U.S. Cl. .......................... 435/7.1; 435/7.2; 435/325; 530/300; 530/350

(58) Field of Classification Search .................. None
See application file for complete search history.

(56) References Cited

U.S. PATENT DOCUMENTS 4,582,790 A 4/1986 Auerbach et al.

6,242,579 B1 6/2001 Lawmann et al.
7,122,178 B1 * 10/2006 Simmons et al. ........... 424/93.1

OTHER PUBLICATIONS

Quesenberry et al. "Hematopoietic stem cells, progenitor cells, and cytokines", pp. 153-174, Williams Hematology, Sixth Edition, New York: McGraw-Hill, 2001.*
Tavian et al. The vascular wall as a source of stem cells. Ann NY Acad Sci 1044 : 41-50, 2005.*
Pittenger et al. Multilineage potential of adult human mesenchymal stem cells. Science 284: 143-147, 1999.*
Li et al. Identification and isolation of candidate human keratinocyte stem cells based on cell surface phenotype. Proc Natl Acad Sci USA 95: 3902-3907, 1998.*
Haruna et al. Identification of bipotential progenitor cells in human liver development. Hepatology 23: 476-481, 1996.*
Ramshaw et al., "Monoclonal antibody BB9 raised against bone marrow stromal cells identifies a cell-surface glycoprotein expressed by primitive human hemopoietic progenitors," *Experimental Hematology* 29:982-992 (2001).
Database Medline, U.S. National Library of Medicine, Bethesda, MD, USA, (Feb. 1989), Danilov S. et al., "Monoclonal antibodies to angiotensin-converting enzyme: a powerful tool for lung and vessel studies." Journal of Molecular and Cellular Cardiology, Feg. 1989, vol. 21, Suppl. 1, pp. 165-170 (abstract only).
Database Biosis, Biosciences Information Service, Philadelphia, PA, USA, 1985, Takada et al., "Angiotensin converting enzyme a possible histologic indicator for human renal cell carcinoma" Cancer, vol. 56, No. 1, 1985, pp. 130-133 (abstract only).

* cited by examiner

*Primary Examiner*—Bridget E Bunner
(74) *Attorney, Agent, or Firm*—Karl Bozicevic; Bozicevic, Field & Francis LLP

(57) ABSTRACT

The present invention relates to the identification of a specific population of cell types, in particular somatic stem cells including haematopoietic stem cells, mesenchymal stem cells and keratinocyte stem cells. The invention also provides for methods of isolation and uses of the stem cells. Derived from the methods of the present invention, there is provided a method of identifying a stem cell comprising the steps of: obtaining a cell sample including stem cells; detecting the presence of angiotensin converting enzyme (ACE) or a fragment thereof on a cell; and identifying the stem cells having ACE or a fragment thereof.

25 Claims, 8 Drawing Sheets

IDENTIFICATION AND ISOLATION OF SOMATIC STEM CELLS AND USES THEREOF

Figure 1:
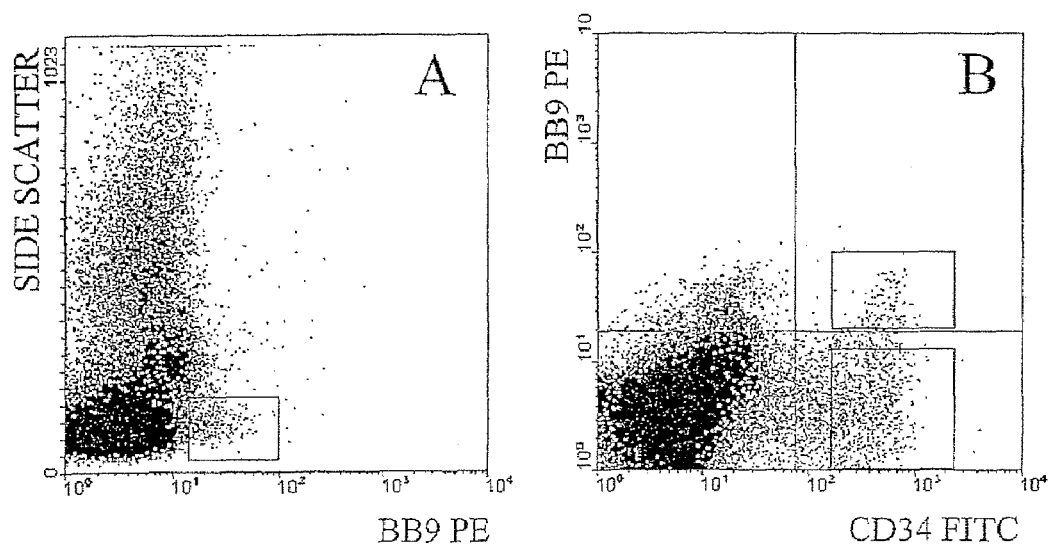

The present invention relates to the identification of a specific population of cell types, in particular somatic stem cells including haematopoietic stem cells, mesenchymal stem cells and keratinocyte stem cells. The invention also provides for methods of isolation and uses of the stem cells derived from the methods.

INTRODUCTION

There exist a strong interest in identifying specific cell types in an effort to gain enriched populations of the cells. Having possession of an enriched population may allow for a better understanding of the specific cell types or even provide uses in various situations including transplantation, gene therapy, treatment of disease including cancers such as leukaemias, neoplastic cancers including breast cancers, or repair of tissues and skin.

Stem cells and the isolation and identification of such cells provides many advantages. These cells are defined as cells which are not terminally differentiated, which can divide without limit, and divide to yield cells that are either stem cells or which irreversibly differentiate to yield a new type of cell. Those stem cells which give rise to a single type of cell are called unipotent cells; those which give rise to many cell types are called pluripotent cells.

Stem cells are by definition present in all self-renewing tissues. These cells are believed to be long-lived, have a great potential for cell division and are ultimately responsible for the homeostasis of steady-state tissues. Stem cells possess many of the following properties: they are relatively undifferentiated, ultrastructurally and biochemically; they have a large proliferative potential and are responsible for the long term maintenance and regeneration of tissue; they are normally "slow-cycling", presumably to conserve their proliferative potential and to minimize DNA errors that could occur during replication; they can be stimulated to proliferate in response to wounding and to certain growth stimuli; they are often located in close proximity to a population of rapidly proliferating cells corresponding to the transient amplifying cells ("TA") in the scheme of (1) stem cell to (2) TA cell to (3) terminally differentiated cell; and they are usually found in well protected, highly vascularized and innervated areas.

Positive identification of stem cells has been difficult because there are no known immunological or biochemical markers specific for somatic stem cells. Since they are normally "slow cycling", methods of identification are limited.

Stem cells are important targets for gene therapy, where the inserted genes promote the health of the individual into whom the stem cells are transplanted. In addition, the ability to isolate stem cells can serve in the treatment of lymphomas and leukaemias, as well as other neoplastic conditions where the stem cells are purified from tumor cells in the bone marrow or peripheral blood, and reinfused into a patient after myelosuppressive or myeloablative chemotherapy. Thus, there have been world-wide efforts toward isolating stem cells in substantially pure form.

Stem cells constitute only a small percentage of the total number of pluripotent cells. Pluripotent cells are identifiable by the presence of a variety of cell surface "markers." Such markers can be either specific to a particular lineage or progenitor cell or be present on more than one cell type. Currently, it is not known how many of the markers associated with differentiated cells are also present on stem cells.

In view of the small proportion of the total number of cells in the bone marrow or peripheral blood which are stem cells, the uncertainty of the markers associated with the stem cell as distinct from more differentiated cells, and the general difficulty in assaying for stem cells biologically, the identification and purification of stem cells has been elusive.

Somatic stem cells give rise to cells which ultimately contribute to various parts of the plant or animal. Generally the somatic cells can be divided into haematopoietic, mesenchymal or keratinocyte stem cells.

Mammalian hematopoietic cells are responsible for an extraordinarily diverse range of activities. They are divided into several lineages, including lymphoid, myeloid and erythroid. The lymphoid lineage, comprising B cells and T cells, produces antibodies, regulates cellular immunity, and detects foreign agents such as disease-causing organisms in the blood. The myeloid lineage, which includes monocytes, granulocytes, and megakaryocytes, monitors the blood for foreign bodies, protects against neoplastic cells, scavenges foreign materials, and produces platelets. The erythroid lineage includes red blood cells, which carry oxygen.

The relative paucity of hematopoietic stem cells has prevented extensive research on stem cells and hematopoietic differentiation in general. The ready availability of a cell population enriched in hematopoietic stem cells would make possible the identification of biological modifiers affecting stem cell behavior. For example, there may be as yet undiscovered growth factors associated with (1) early steps of dedication of the stem cell to a particular lineage; (2) the prevention of such dedication; and (3) the ability to control stem cell proliferation.

The availability of sufficient numbers of stem cells in an enriched population would also be extremely useful, for example, in reconstituting hematopoiesis in patients undergoing treatments which destroy stem cells, such as cancer chemotherapy.

Mesenchymal stem cells (MSCs) are the formative pluripotential cells found inter alia in bone marrow, blood, dermis and periosteum that are capable of differentiating into more than one specific type of mesenchymal or connective tissues (i.e. the tissues of the body that support the specialized elements; e.g. adipose, osSEQus, stroma, cartilaginous, elastic and fibrous connective tissues) depending upon various influences from bioactive factors, such as cytokines. Human mesenchymal stem cells (hMSCs) are reactive with certain monoclonal antibodies, known as SH2, SH3 and SH4.

Keratinocyte stem cells give rise to skin cells and cells of the epidermis. They are particularly useful in the treatment of ulcers, acute wounds and grafting of acute wounds.

However, identification of these specific cell types by cell surface markers has generally proven to be the best means of identification. The identification of additional cell surface antigens would clearly be of major value in the identification, isolation and further characterization of candidate stem cells.

Accordingly, it is an object of the present invention to overcome or alleviate some of the problems of the prior art.

SUMMARY OF THE INVENTION

In one aspect of the present invention there provided a method of identifying a stem cell comprising the steps of
  obtaining a cell sample including stem cells;
  detecting the presence of a peptide sequence having the sequence LFQELQPLYL (SEQ ID NO:1) or an equivalent thereof; and
  identifying the stem cells having the sequence or equivalent thereof.

In another aspect of the present invention here provided a method of identifying a stem cell comprising the steps of
obtaining a cell sample including stem cells;
detecting the presence of a peptide sequence having the sequence EADDFFTS (SEQ ID NO:2) or an equivalent thereof; and
identifying the stem cells having the sequence or equivalent thereof.

The peptide sequences described herein as SEQ ID NO:1 or SEQ ID NO:2 have been found to be expressed specifically on stem cells. The sequence may be a portion of a larger protein or be a sequence expressed by the stem cells. These sequences may used alone or in combination to identify or isolate stem cells.

Applicants have found that angiotension converting enzyme (ACE) is expressed in stem cells. ACE acts on converting angiotensin-I to angiotensin-II. Angiotensin-II increases blood pressure and is considered a main cause of essential hypertension. The sequences described may be a portion of ACE.

Accordingly, in another aspect of the present invention there is provided a method of identifying a stem cell comprising the steps of:
obtaining a cell sample including stem cells;
detecting the presence of angiotensin converting enzyme (ACE) or a fragment thereof on a cell; and
identifying the stem cells having ACE or a fragment thereof.

Any means of identifying the ACE may be used. However, in a preferred aspect of the present invention there is provided a method of identifying a stem cell comprising the steps of:
obtaining a cell sample including stem cells;
combining the sample with an antibody for angiotensin converting enzyme (ACE);
detecting the presence of ACE or a fragment thereof; and
identifying the stem cells having ACE by detecting the presence of the antibody on the stem cells.

Preferably, the antibody is any antibody specific for ACE. The antibody used in the present invention encompasses any antibody or fragment thereof, either native or recombinant, synthetic or naturally-derived, monoclonal or polyclonal which retains sufficient specificity to bind specifically to the ACE or a fragment thereof which is indicative of ACE. Preferably, the antibody is BB9 ACE antibody.

The present invention also encompasses a method for obtaining a cell population enriched in stem cells comprising the steps of
obtaining a cell population comprising stem cells;
detecting the presence of ACE or a fragment thereof on a cell; and
selecting for cells which are identified by the presence of ACE on the cell.

In a preferred aspect of the present invention there is provided a method of obtaining a cell population enriched in haematopoietic stem cells comprising the steps of:
obtaining cell populations comprising stem cells;
combining the cell population with an antibody for ACE; and
selecting for cells which are identified by the presence of ACE on the cell.

Similarly, in another preferred embodiment, there is provided a method of removing stem cells from a population comprising the steps of
obtaining a cell population comprising stem cells;
detecting the presence of ACE or a fragment thereof or a cell; and
selecting out those cells which are identified by the presence of ACE on the cell.

The methods described herein may also be used to isolate stem cells from cell populations or measure stem cell content in such populations.

Once a stem cell is isolated or identified, they may be used in methods of treating or diagnosing stem cell related conditions.

Preferably, the stem cell isolated is a haematopoietic stem cell, mesenchymal stem cell or a keratinocyte stem cell. However, other cells including neuronal, hepatic and pancreatic cells may also be included. Most preferably, the stem cell is a haematopoietic stem cell.

Once the stem cell population is isolated, further isolation techniques may be employed to isolate subpopulations with the stem cells. Specific markers for mesenchymal or keratinocyte cells may be used to identify and isolate the various cell lineages.

FIGURES

FIG. 1 shows expression of CD34 and BB9 on normal human bone marrow. Panel A displays expression of BB9 with respect to the perpendicular light scatter (side scatter) on BMMNC. The rectangular region surrounds cells that are BB9$^+$ and exhibit low side scatter. Panel B displays the expression of CD34 and BB9. The rectangular regions defining CD34$^+$BB9$^+$ (upper right quadrant) and CD34$^+$BB9$^-$ cells (lower right quadrant) were typical of those used for isolation of cells by FACS used for clonogenic and pre-CFU assays.

Figure 2:
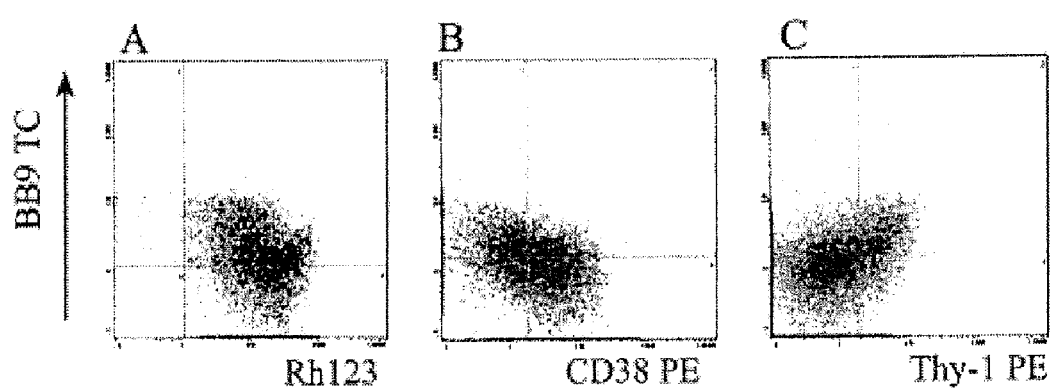

FIG. 2 shows that BB9 preferentially binds to primitive hematopoietic progenitors. Three colour flow cytometric analysis of Rh123 retention (panel A), CD38 (panel B) and CD90 (Thy-1: panel C) expression relative to the binding of BB9 on BM derived CD34$^+$ cells. Highest levels of BB9 antigen expression are present on CD34$^+$ BMMNC, which co-express CD90, show low to undetectable CD38 expression and are Rh123$^{dull}$. Each plot was generated from at least 10$^4$ CD34$^+$ events collected as list mode data.

Figure 3:
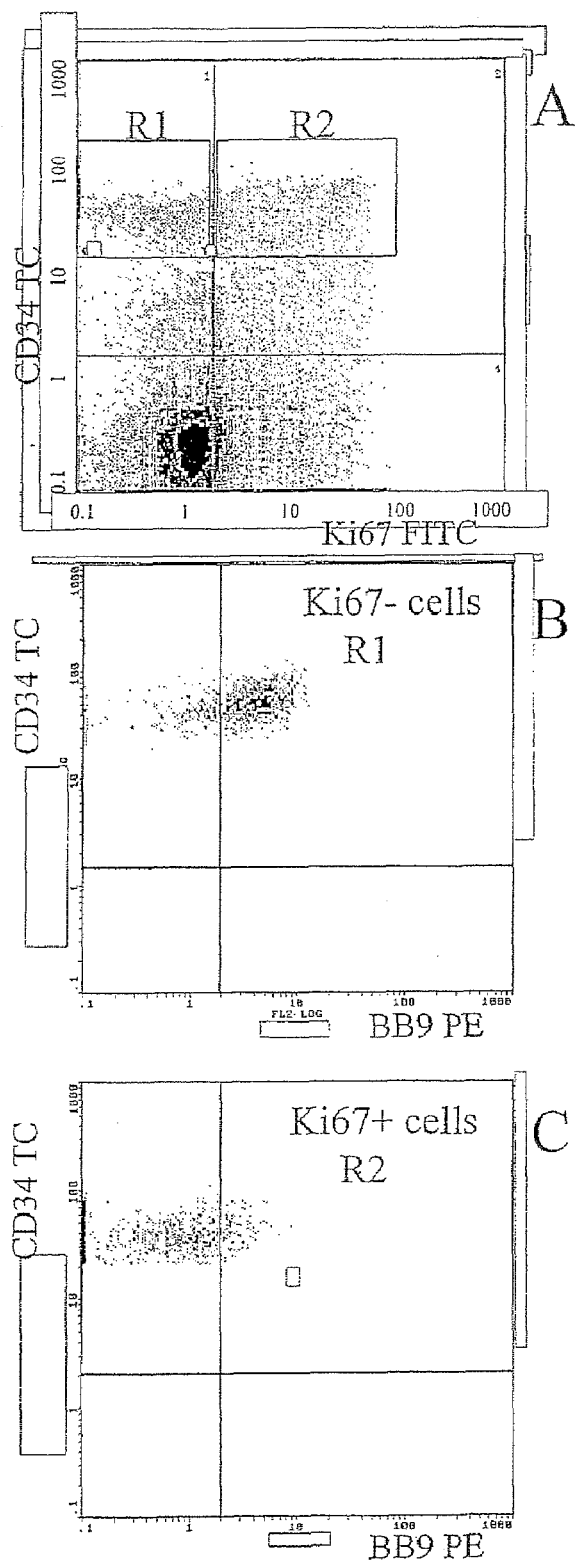

FIG. 3 shows that BB9 identifies quiescent (G$_0$) cells in the CD34$^+$ population in adult human BM. Three colour flow cytometric analysis of Ki67, CD34 and BB9 expression was performed on adult BM. Panel A depicts Ki67 and CD34 expression of BMMNC. Region 1 (R1) identifies CD34$^+$ cells that exhibit low/negative Ki67 expression, whereas R2 identifies CD34$^+$ cells with high Ki67. Panel B displays expression of BB9 by those cells defined by R1 (Ki67 low: quiescent cells) and Panel C displays BB9 expression of Ki67 positive (proliferating) cells.

Figure 4:
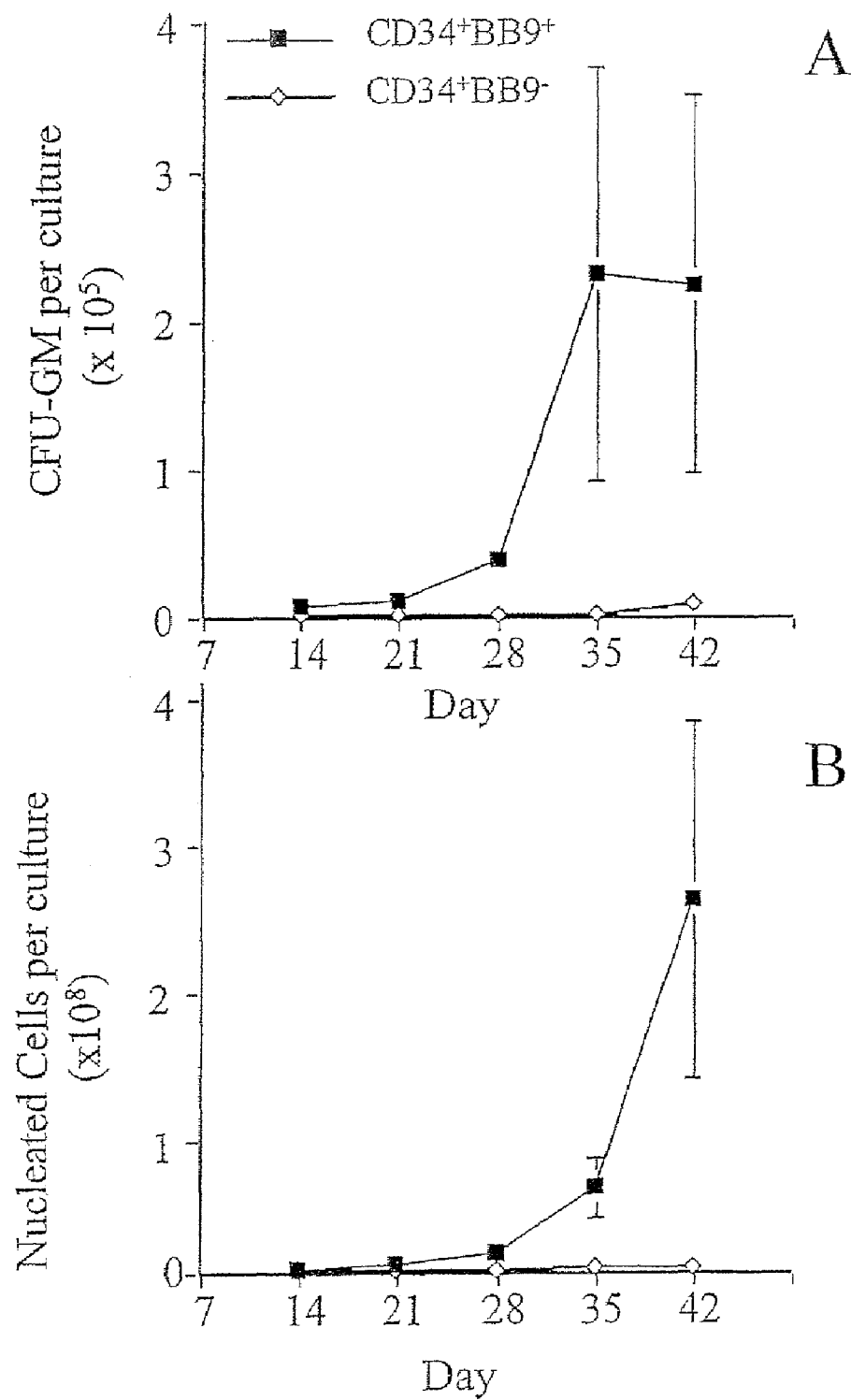

FIG. 4 shows CFU-GM and nucleated cell generation from CD34$^+$BB9$^+$ and CD34$^+$BB9$^-$ BM cells in pre-CFU culture. Generation of CFU-GM (panel A) and nucleated cells (panel B) and from 1000 CD34$^+$BB9$^+$ or CD34$^+$BB9$^-$ BM cells in pre-CFU culture stimulated with 4 HGF (IL-3, IL-6, SCF and G-SCF). At day 14 and at weekly intervals thereafter, the cultures were subjected to 1 in 10 splits and refed with fresh medium and HGF. The mean and standard error from 10 separate experiments with different sources of BM are presented.

Figure 5:
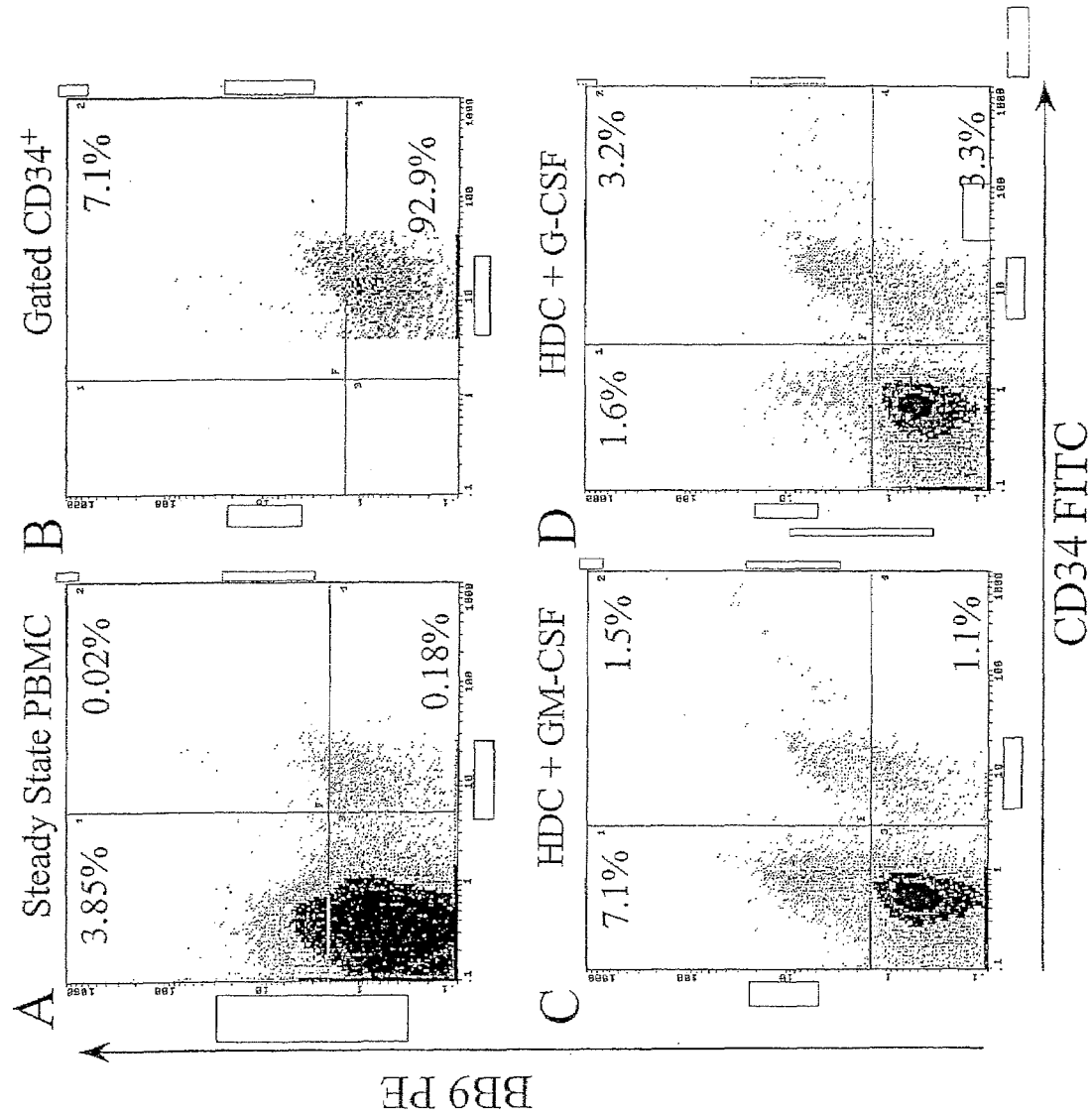

FIG. 5 shows an expression of CD34 and BB9 on steady state and mobilized peripheral blood cells. Peripheral blood mononuclear cells from normal adult volunteer donors, representing steady state hematopoiesis (panels A and B), and patients mobilised with high dose cyclophosphamide (HDC)+G-CSF (panel C) or HDC+GM-CSF (panel D) were immunolabelled with antibodies to CD34 and BB9. Each panel displays the expression of CD34 (horizontal axis) and BB9 (vertical axis) and the numbers within each quadrant represents the proportion of cells within the respective quadrant. The dot plot shown within panel B displays CD34 and BB9 expression for CD34+ cells from steady state blood. These data are representative of at least 4 samples of the different cell sources.

Figure 6:
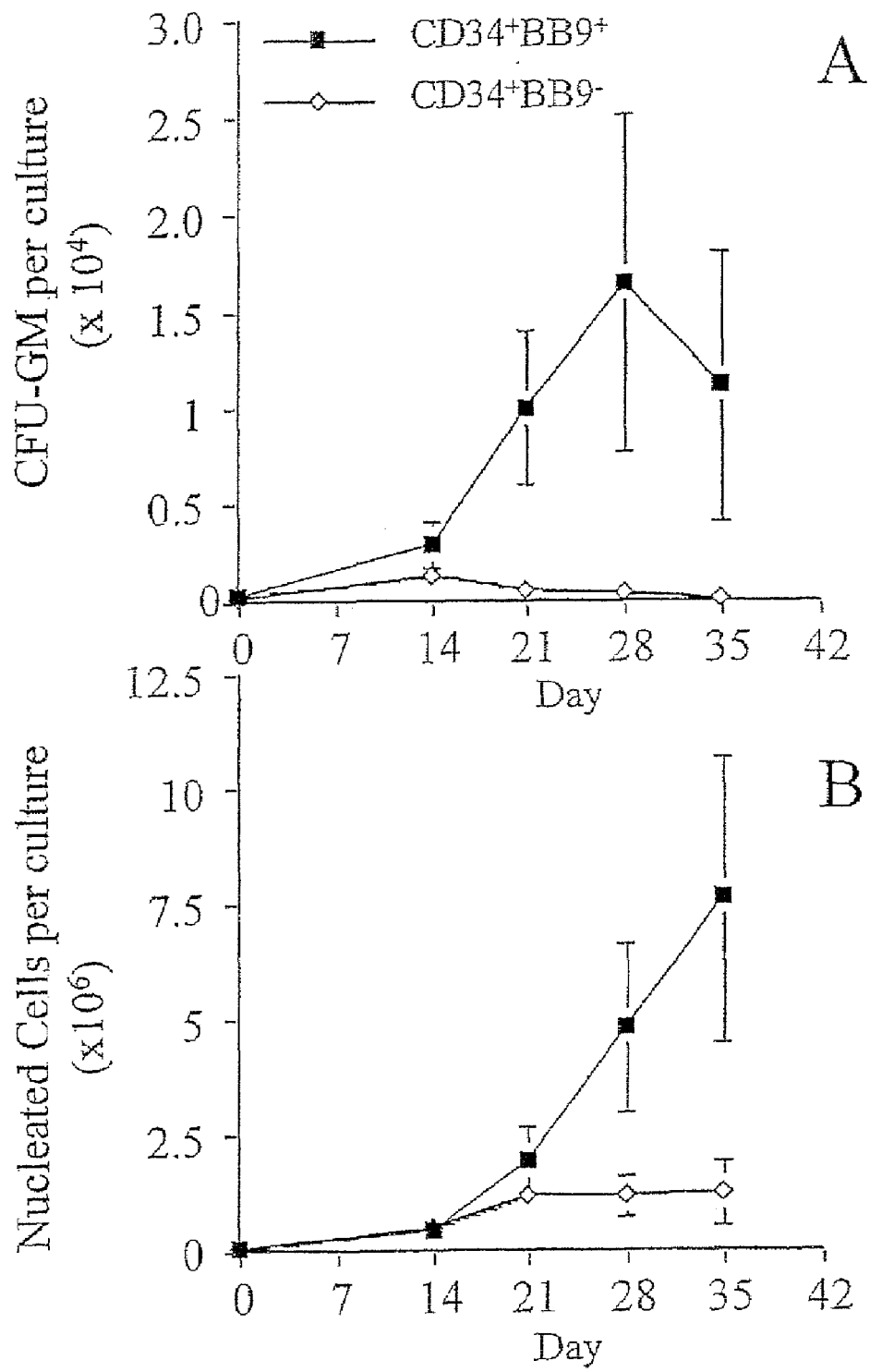

FIG. 6 shows CFU-GM and nucleated cell generation from mobilized PB CD34+BB9+ and CD34+BB9− cells in pre-CFU culture. Panels A and B show generation of CFU-GM and nucleated cells, respectively, from 1000 CD34+BB9+ or CD34+BB9− MPB cells in pre-CFU culture stimulated with 4 HGF (IL-3, IL-6, SCF and G-SCF). At day 14 and at weekly intervals thereafter, the cultures were subjected to 1 in 10 splits and refed with fresh medium and HGF. At each time point, the mean and standard error for the combined data from 6 patients, 3 mobilised with HDC+GM-CSF and 3 with HDC+G-CSF are presented.

Figure 7:
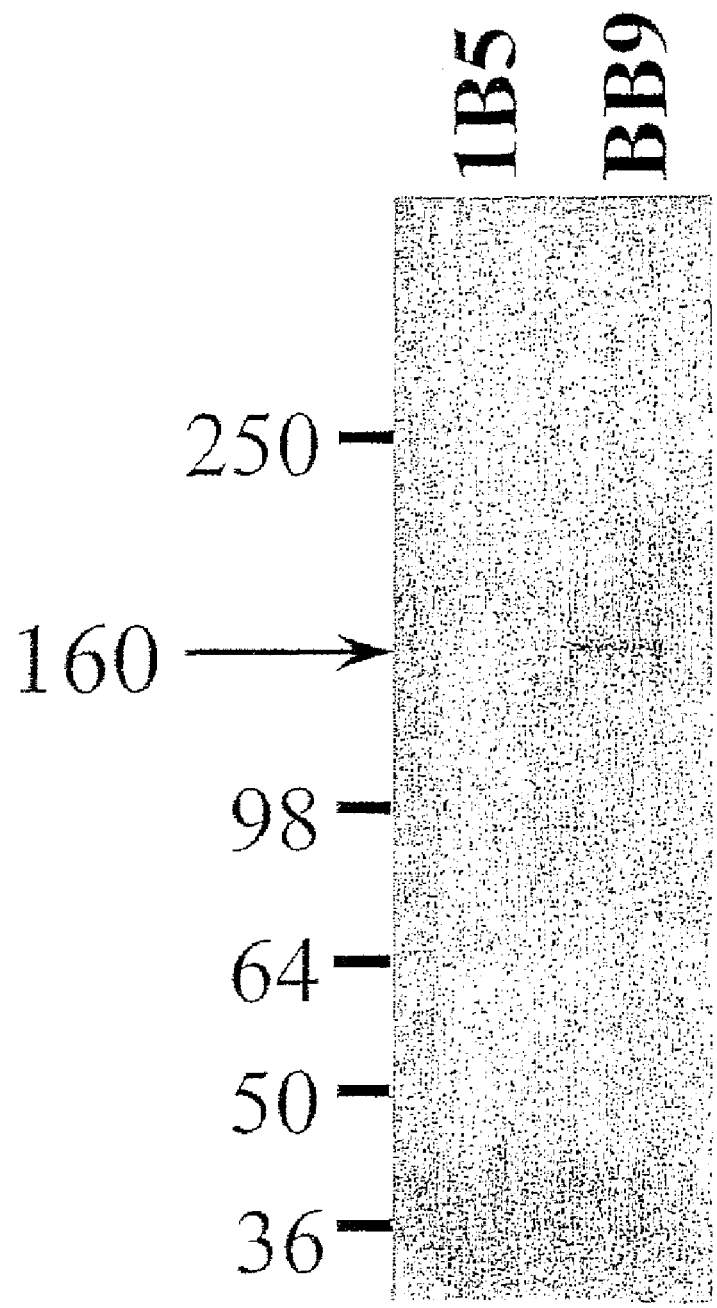

FIG. 7 shows that BB9 Identifies a Protein of 160 kDa. Immunoprecipitation analysis of surface $^{125}$I labelled UT7 cells. Lane 1, negative control antibody. Lane 2, BB9; BB9 immunoprecipitated a protein of 160 kDa. The positions of molecular weight markers are shown at the left.

Figure 8:
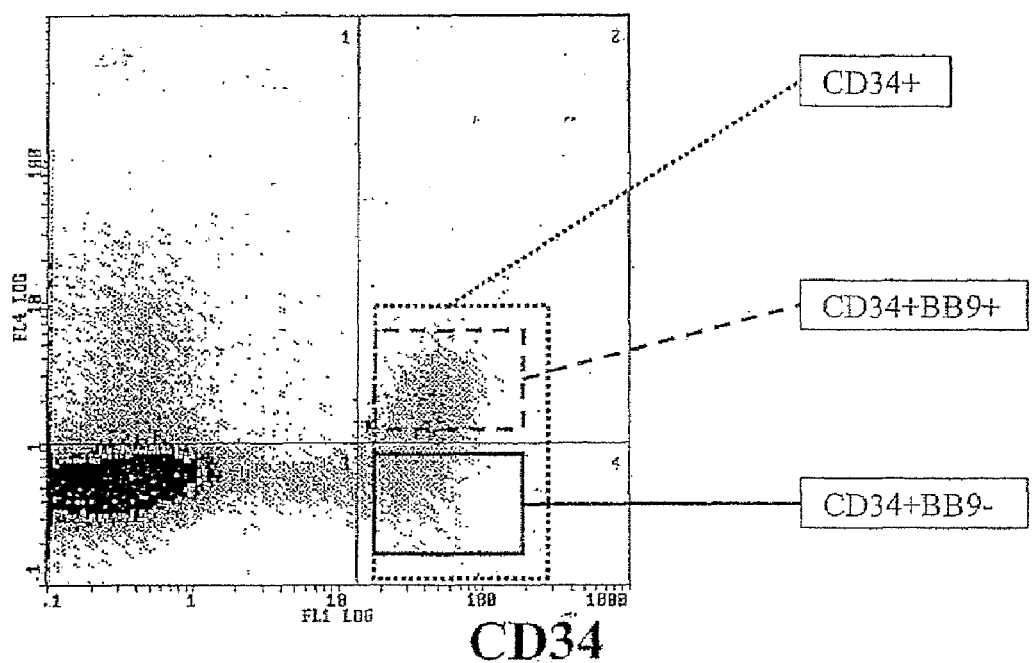

FIG. 8 shows CD34+BB9+ cells engraft NOD/SCID Mice.

DESCRIPTION OF THE INVENTION

In one aspect of the present invention there provided a method of identifying a stem cell comprising the steps of
   obtaining a cell sample including stem cells;
   detecting the presence of a peptide sequence having the sequence LFQELQPLYL (SEQ ID NO:1) or an equivalent thereof; and
   identifying the stem cells having the sequence or equivalent thereof.

In another aspect of the present invention here provided a method of identifying a stem cell comprising the steps of
   obtaining a cell sample including stem cells;
   detecting the presence of a peptide sequence having the sequence EADDFFTS (SEQ ID NO:2) or an equivalent thereof; and
   identifying the stem cells having the sequence or equivalent thereof.

The peptide sequences described herein as SEQ ID NO:1 or SEQ ID NO:2 have been found to be expressed specifically on stem cells. The sequence may be a portion of a larger protein or be a sequence expressed by the stem cells.

The term "equivalent" thereof as used herein means a sequence which functions in a similar way but may have deletions, additions or substitutions that do not substantially change the activity or function of the sequence. Therefore, at least one amino acid may be deleted, added or substituted into the peptide sequence without substantially changing the functionality of the sequence. Hence, the peptide sequence with changes should still be detectable for identification of the stem cells.

In another aspect of the present invention there is provided a method of identifying a stem cell comprising the steps of:
   obtaining a cell sample including stem cells;
   detecting the presence of angiotensin converting enzyme (ACE) or a fragment thereof on a cell; and
   identifying the stem cells having ACE or a fragment thereof.

Applicants have found that angiotension converting enzyme (ACE) is expressed in stem cells. ACE acts on converting angiotensin-I to angiotensin-II. Angiotensin-II increases blood pressure and is considered a main cause of essential hypertension.

ACE, also referred to as peptidyl dipeptidase A (EC 3.4.15.1) and kininase II is a metallopeptidase, more particularly a zinc peptidase which hydrolyses angiotensin I and other biologically active polypeptides, such as kinins, e.g., bradykinin. Bradykinin is a vasodilator, which acts at least in part by inducing release of vasodilator prostaglandins, and which is inactivated upon hydrolysis by ACE. Thus, ACE increases blood pressure at least in part by producing angiotensin II, a vasoconstrictor, and by inactivating bradykinin, a vasodilator. Bradykinin is also involved in other biological activities including mediation of pain and inflammatory reactions.

However, the enzyme has not previously been connected to stem cells nor for their identification.

ACE or a fragment of ACE may be detected on the stem cell. Preferably the ACE molecule is detected. However, fragments of the ACE molecule may also be indicative of ACE. Such fragments may include peptide sequences having the sequence encoded by SEQ ID NO:1 or SEQ ID NO:2 or an equivalent thereof.

Applicants have found that the SEQ ID NO:1 and SEQ ID NO:2 are found within the ACE amino acid sequence and were subsequently found to be identified by ACE antibodies.

Throughout the description and claims of this specification, the word "comprise" and variations of the word, such as "comprising" and "comprises", is not intended to exclude other additives, components, integers or steps.

The stem cells of the present invention and described herein include all stem cells which are essentially undifferentiated cells in an embryo or adult which can undergo unlimited division and can give rise to one or several cell types. It is preferred that the stem cells of the present invention include, but are not limited to, somatic stem cells. These may be selected from the group including haematopoietic stem cells, mesenchymal stem cells, keratinocyte stem cells neuronal, hepatic and pancreatic cells. Most preferably, they are haematopoietic stem cells which can differentiate to stem cells of a lymphoid, myeloid or erythroid lineage. However applicants find that the method is also useful for distinguishing mesenchymal and keratinocyte stem cells.

The sample of stem cells may originate from any source including an embryonic or adult source. Preferably, the stem cell source is from the bone marrow including iliac crests, tibiae, femors, spine, periosteum, endosteum or other bone cavities, blood, embryonic yolk sac, fetal liver, spleen, peripheral, blood, skin, dermis, liver, brain, pancreas or kidney.

The sample may be a tissue sample or a cell suspension or cells derived from either source grown in vitro which allows for interaction of a marker for ACE to identify the stem cells.

For isolation of bone marrow, an appropriate solution can be used to flush the bone, including, but not limited to, salt solution, conveniently supplemented with fetal calf serum (FCS) or other naturally occurring factors, in conjunction with an acceptable buffer at low concentration, generally from about 5-25 mM. Convenient buffers include, but are not limited to, HEPES, phosphate buffers and lactate buffers. Otherwise bone marrow can be aspirated from the bone in accordance with conventional techniques.

The method of detecting ACE or the specific sequences SEQ ID NO:1 or SEQ ID NO:2 will be dependent upon the type of sample including the stem cells. Generally the sample is exposed or combined with a marker for ACE or the sequences in a manner which facilitates the marker interaction with the cells. For example, where the sample is a cell suspension as in a blood sample, the marker may simply be added to the cell suspension. This is applicable where the marker is intended to physically identify ACE or the sequences.

The marker for ACE or the sequences may include any means which identifies ACE or the sequences, preferably it is a marker which identifies ACE or the sequences on a cell surface which includes but is not limited to antibodies to ACE or the sequences, agonists and antagonists against ACE or the sequences, nucleic acid detection systems which can detect expression of ACE or the sequences either by the presence of DNA, RNA, mRNA or ACE protein, and enzymatic, fluorescence or colourimetric assays for ACE. The method of detection will be apparent to the skilled addressee for the type of marker selected.

The marker may include the addition of labels to enhance the identification of the marker. For instance, fluorescence, radioactivity or enzymatic markers familiar to the skilled addressee may be linked to the marker to enhance detection.

In a preferred aspect of the present invention there is provided a method of identifying a stem cell comprising the steps of:
  obtaining a cell sample including stem cells;
  combining the sample with an antibody for angiotensin converting enzyme (ACE);
  detecting the presence of ACE or a fragment thereof; and
  identifying the stem cells having ACE by detecting the presence of the antibody on the stem cells.

Preferably, the antibody is any antibody specific for ACE. The antibody used in the present invention encompasses any antibody or fragment thereof, either native or recombinant, synthetic or naturally-derived, monoclonal or polyclonal which retains sufficient specificity to bind specifically to the ACE or a fragment thereof which is indicative of ACE. As used herein, the terms "antibody" or "antibodies" include the entire antibody and antibody fragments containing functional portions thereof. The term "antibody" includes any monospecific or bispecific compound comprised of a sufficient portion of the light chain variable region and/or the heavy chain variable region to effect binding to the epitope to which the whole antibody has binding specificity. The fragments can include the variable region of at least one heavy or light chain immunoglobulin polypeptide, and include, but are not limited to, Fab fragments, F(ab')$_2$ fragments, and Fv fragments.

The recombinant antibody can be produced by any recombinant means known in the art. Such recombinant antibodies include, but are not limited to, fragments produced in bacteria and non-human antibodies in which the majority of the constant regions have been replaced by human antibody constant regions. In addition, such "humanized" antibodies can be obtained by host vertebrates genetically engineered to express the recombinant antibody.

In addition, the monospecific domains can be attached by any method known in the art to another suitable molecule compound. The attachment can be, for instance, chemical or by genetic engineering.

The antibodies can be conjugated to other suitable molecules and compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein is thiocyanate, tetramethylrhodamine isothiocyanate, phycoerythrin, allophycocyanins and Texas Red. For additional fluorochromes that can be conjugated to antibodies see Haugland, R. P. Molecular Probes: Handbook of Fluorescent Probes and Research Chemicals (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m, $^{125}$I and amino acids comprising any radionuclides, including, but not limited to $^{14}$C, $^3$H and $^{35}$S.

The ACE antibodies may be obtained by methods known in the art for production of antibodies or functional portions thereof. Specific methods used are described in the Examples presented herein although any method known in the art of antibody production can be used. Such methods include, but are not limited to, separating B cells with cell-surface antibodies of the desired specificity, cloning the DNA expressing the variable regions of the light and heavy chains and expressing the recombinant genes in a suitable host cell. Standard monoclonal antibody generation techniques can be used wherein the antibodies are obtained from immortalized antibody-producing hybridoma cells. These hybridomas can be produced by immunizing animals with stem cells, and fusing B lymphocytes from the immunized animals, preferably isolated from the immunized host spleen, with compatible immortalized cells, preferably a B cell myeloma.

ACE antibodies may be obtained from any source. They may be commercially available. Effectively, any means which detects the presence of ACE on the cells is with the scope of the present invention.

In a further preferred aspect of the present invention there is provided a method of identifying a stem cell comprising the steps of:
  obtaining a sample including stem cells;
  combining the sample with antibody BB9 specific for angiotensin converting enzyme (ACE);
  detecting the presence of BB9 or a fragment thereof;
  identifying the stem cells by detecting the presence of the antibody BB9 on the stem cells.

A monoclonal antibody (MAb), BB9, was identified by the Applicants based on its binding to stromal cells, a minor subpopulation of mononuclear cells in adult human BM and corresponding lack of reactivity with leukocytes in PB. BB9 bound to a minor subpopulation of BM CD34$^+$ cells characterized by high level CD34 antigen and Thy-1 expression, low-absent expression of CD38, low retention of Rhodamine 123 and quiescent cycle status as evidenced by lack of labeling with Ki67. CD34$^+$BB9$^+$ cells, in contrast to CD34$^+$BB9$^-$ cells, demonstrated a capacity to preferably sustain hematopoiesis in pre-CFU culture stimulated by the combination of IL-3, IL-6, G-CSF and SCF. BB9 also demonstrated binding to CD34$^+$ cells from mobilised PB.

BB9 was identified during initial antibody screening by its apparent lack of binding to mononuclear cells in adult BM and peripheral blood (PB) and, on subsequent flow cytometric analysis, by its binding to a minor subpopulation of BM CD34$^+$ cells. These cells have been shown to sustain long term hematopoiesis in stromal cell free liquid culture and by phenotypic analysis to express markers characteristic of primitive hematopoietic progenitor cells.

The isolation of this antibody is specifically described herein the examples.

BB9 is preferably used to identify haematopoietic stem cells. However, applicants have found that it is also useful for identifying mesenchymal stem cells and keratinocyte stem cells.

The method outlined herein is particularly useful for identifying stem cells from a population of cells. However, additional markers may be used to further distinguish subpopulations within the general stem cell population.

For instance, mesenchymal stem cells can be further identified by markers including, but not limited to, STRO-1, SH2, SH3 and SH4. These markers may be used singularly or in combination to identify mesenchymal stem cells.

Keratinocyte stem cells may be identified by markers including but not limited to, cytokeratin 14, alpha-6 integrin (CD49F) and CD71. These markers may be used separately or in combination to identify keratinocyte stem cells.

The step of using additional markers may be applied separately or in combination with an ACE marker.

In another aspect of the present invention, there is provided a method for obtaining a cell population enriched in stem cells comprising the steps of
  obtaining a cell population comprising stem cells;
  detecting the presence of ACE or a fragment thereof on a cell; and
  selecting for cells which are identified by the presence of ACE on the cell.

The present invention thus encompasses methods of enriching a population for stem cells. The methods involve combining a mixture of stem cells preferably with an antibody that recognizes and binds to ACE under conditions which allow the antibody to bind to ACE and separating the cells recognized by the antibody to obtain a population substantially enriched in stem cells. However, other forms of identification of ACE may be used as described above. The methods can be used as a diagnostic assay for the number of stem cells in a sample. The cells and antibody are combined under conditions sufficient to allow specific binding of the antibody to ACE and the stem cells which are then quantitated. The stem cells can be isolated or further purified.

As discussed above the cell population may be obtained from any source of stem cells including those samples discussed above.

The detection for the presence of ACE may be conducted in any way to identify ACE on cells. Preferably the detection is by use of a marker for ACE. The marker for ACE may be any of the markers discussed above. However, antibodies to ACE are particularly useful as a marker for ACE. More preferably the antibody is BB9.

As discussed above, ACE or a fragment of ACE may be detected. Preferably the whole molecule ACE will be detected or a fragment corresponding to SEQ ID NO:1 or SEQ ID NO:2 or equivalents thereof can be detected.

Various techniques can be employed to separate or enrich the cells by initially removing cells of dedicated lineage. Monoclonal antibodies are particularly useful for identifying cell lineages and/or stages of differentiation. The antibodies can be attached to a solid support to allow for crude separation. The separation techniques employed should maximize the retention of viability of the fraction to be collected. Various techniques of different efficacy can be employed to obtain "relatively crude" separations. The particular technique employed will depend upon efficiency of separation, associated cytotoxicity, ease and speed of performance, and necessity for sophisticated equipment and/or technical skill.

Procedures for separation or enrichment can include, but are not limited to, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique.

The use of separation or enrichment techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye, Hoescht 33342).

Techniques providing accurate separation include, but are not limited to, FACS, which can have varying degrees of sophistication, e.g., a plurality of color channels, low angle and obtuse light scattering detecting channels, impedence channels, etc.

In a first separation, typically starting with about $1 \times 10^{8-9}$, preferably at about $5 \times 10^{8-9}$ cells, ACE antibody can be labeled with one fluorochrome, while the antibodies for the various dedicated lineages, can be conjugated to at least one different fluorochrome. While each of the lineages can be separated in a separate step, desirably the lineages are separated at the same time as one is positively selecting for ACE and/or other stem cell markers. The cells can be selected against dead cells, by employing dyes associated with dead cells (including but not limited to, propidium iodide (PI)). Preferably, the cells are collected in a medium comprising 2% FCS.

While it is believed that the particular order of separation is not critical to this invention, the order indicated is preferred. Preferably, cells are initially separated by a coarse separation, followed by a fine separation, with positive selection with ACE antibody.

In a preferred aspect of the present invention there is provided a method of obtaining a cell population enriched in haematopoietic stem cells comprising the steps of:
  obtaining cell populations comprising stem cells;
  combining the cell population with an antibody for ACE; and
  selecting for cells which are identified by the presence of ACE on the cell.

Preferably the antibody is BB9. However, other antibodies to ACE would be equally effective. Any separation methods employing antibodies to isolate cells may be utilised and are familiar to the skilled addressee.

To further enrich for any cell population, specific markers for those cell populations may be used. For instance, specific markers for mesenchymal cells including but not limited to STRO-1, SH2, SH3 and SH4 may be used to enrich for or against these cells.

Similarly, specific markers for keratinocyte stem cells including but not limited to cytokeratin 14, alpha-6 integrin (CD49F) and CD71 may be used to enrich for or against those cells.

These markers may also be used to enrich for haematopoietic stem cells by removing or selecting out mesenchymal or keratinocyte stem cells.

Similarly, in another preferred embodiment, there is provided a method of removing stem cells from a population comprising the steps of
  obtaining a cell population comprising stem cells;
  detecting the presence of ACE or a fragment thereof or a cell; and
  selecting out those cells which are identified by the presence of ACE on the cell.

In the same manner as the enrichment, the use of ACE may be reversed to provide a population substantially devoid of stem cells. The method used above to select for those cells expressing ACE can be used to select out the same cells leaving a population stripped of the stem cells.

Preferably, ACE is detected by using an antibody to ACE or a fragment thereof. The fragment may be encoded by SEQ ID NO:1 or SEQ ID NO:2 or an equivalent thereof. Preferably the antibody is BB9.

The methods described above can include further enrichment steps for cells by positive selection for other stem cell specific markers. Suitable positive stem cell markers include, but are not limited to, $CD34^+$, $Thy-1^+$, and $c-kit^+$. Preferably the stem cells are human but can be derived from any suitable animal. By appropriate selection with particular factors and the development of bioassays which allow for self-regeneration of stem cells and screening of the stem cells as to their markers, a composition enriched for viable stem cells can be produced for a variety of purposes.

In yet another aspect of the present invention, there is provided a method of isolating a stem cell comprising
    obtaining a cell population comprising stem cells;
    detecting the presence of ACE or a fragment thereof on a cell;
    selecting for those cells which are identified by the presence of ACE on the cell; and
    isolating those cells identified by the presence of ACE.

The stem cells may be isolated by any of the methods used for enrichment as described above providing there is the added step of isolating the stem cell. Useful techniques include magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique. Persons skilled in the art would be familiar with these techniques and can employ any known techniques providing ACE is selected for.

In another preferred aspect there is provided a method of isolating a stem cell comprising
    obtaining a cell population comprising stem cells;
    combining the cell population with an antibody for ACE;
    selecting for those cells which are identified by the antibody for ACE; and
    isolating those cells identified by the antibody.

Preferably the antibody is BB9. However, any antibody presently available which is specific for ACE may be used.

Preferably the stem cell isolated is a haematopoietic stem cell, mesenchymal stem cell or a keratinocyte stem cell. However, other cells including neuronal, hepatic and pancreatic cells may also be included. Most preferably, the stem cell is a haematopoietic stem cell.

Once the stem cell population is isolated, further isolation techniques may be employed to isolate subpopulations with the stem cells. Specific markers described above for mesenchymal or keratinocyte cells may be used to identify and isolate the various cell lineages.

In another aspect there is provided a stem cell isolated by the methods described herein. Preferably, the stem cell is a haematopoietic stem cell, mesenchymal stem cell and/or a keratinocyte stem cell. Most preferably, the stem cell is a haematopoietic stem cell.

The present invention also provides in another aspect, a composition of enriched stem cells. Preferably the enriched stem cells comprise an enrichment of haematopoietic stem cells, mesenchymal stem cell or keratinocyte stem cells.

Where the compositions are enriched for stem cells, these may be used in autologous engraftment. Further, the use of autologous stem cells will avoid graft-versus-host disease. In addition, the cells can be modified by appropriate gene transfer, to correct genetic defects or provide genetic capabilities naturally lacking in the stem cells or their progeny, either as to the individual or as to the stem cells generally. In addition, the stem cell composition can be used to isolate and define factors associated with their regeneration and differentiation.

In yet another aspect of the present invention there is provided a method of measuring stem cell content, said method comprising:
    obtaining a cell population comprising stem cells;
    detecting the presence of ACE or a fragment thereof on a cell with an indicator of ACE;
    selecting for those cells having ACE or a fragment thereof on the cell; and
    quantifying the selected cells relative to the quantity of cells in the cell population prior to selection.

In yet another preferred aspect of the present invention there is provided a method of measuring stem cell content said method comprising
    obtaining a cell population comprising stem cells;
    combining the cell population with an antibody for ACE;
    selecting for those cells which are identified by the antibody for ACE; and
    quantifying the amount of selected cells relative to the quantity of cells in the cell population prior to selection with ACE antibody.

Quantifying the amount of selected stem cells provides for a means of diagnosis of a stem cell associated condition such as, but not limited to leukaemia, carcinomas, or sarcomas or general infections which can cause an increase in stem cell activity, particularly in the haematopoietic stem cell populations, more specifically in the lymphoid lineages of those populations. In particular, the quantitation may provide an indication of the B and T cells which may differentiate from the lymphoid lineages to provide for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

In yet another aspect of the present invention there is provided a composition for detecting stem cells in a population, said composition comprising an indicator of ACE or a fragment thereof and a carrier.

The indicator of ACE may include any detection means which can identify ACE on a stem cell. Preferably the indicator is an antibody to ACE or a fragment thereof. Preferably the antibody is as described above and may be BB9.

The antibody may detect the full molecule of ACE or detect specific peptide sequences contained within ACE. Preferably the antibody will detect peptide sequence SEQ ID NO:1 or SEQ ID NO:2 or an equivalent thereof.

The composition may also comprise additional markers to distinguish mesenchymal and keratinocyte cells. For mesenchymal stem cells the additional markers may include any marker selected from the group including, but not limited to STRO, SH2, SH3 or SH4. For keratinocyte stem cells the markers may be selected from the group including, but not limited to, cytokeratin 14, alpha-6 integrin (CD49F) and CD71.

The invention also provides for methods of diagnosing conditions associated with stem cells by identifying the presence of stem cell types in a cell population. For instance, increased or decreased levels of haematopoietic stem cells may indicate abnormalities in the blood. This may be important in diseases such as leukaemia, similarly, increases may translate to increase in stem cells differentiating to lymphoid lineages including T and B cells indicating infection. Other methods may measure ACE expression on leukemia or other malignancies.

In another aspect of the present invention, there is provided a method of treating a stem cell associated condition comprising administering an effective amount of a composition comprising an enriched population of stem cells and wherein said stem cell is associated with the condition, said enriched population of stem cells being prepared by the methods described herein.

A "stem cell associated condition" as used herein means any condition which results from an interaction with stem cells.

The compositions of the present invention which comprise stem cells isolated by the described methods can find use in a number of ways.

For haematopoietic stem cells, these cells can be used to fully reconstitute an immunocompromised host such as an irradiated host and/or a host subject to chemotherapy; or as a source of cells for specific lineages, by providing for their maturation, proliferation and differentiation into one or more selected lineages by employing a variety of factors, including, but not limited to, erythropoietin, colony stimulating factors, e.g., GM-CSF, G-CSF, or M-CSF, interleukins, e.g., IL-1, -2, -3, -4, -5, -6, -7, -8, etc., or the like, or stromal cells associated with the stem cells becoming committed to a particular lineage, or with their proliferation, maturation and differentiation.

The haematopoietic stem cells can also be used in the isolation and evaluation of factors associated with the differentiation and maturation of hematopoietic cells. Thus, the invention encompasses the use of haematopoietic stem cells in assays to determine the activity of media, such as conditioned media, or to evaluate fluids for cell growth activity, involvement with dedication of particular lineages, or the like.

The haematopoietic stem cells can be used for the treatment of genetic diseases. Thus, the invention encompasses treatment of genetic diseases associated with hematopoietic cells by genetic modification of autologous or allogeneic stem cells to correct the genetic defect. For example, diseases including, but not limited to, beta.-thalassemia, sickle cell anemia, adenosine deaminase deficiency, recombinase deficiency, recombinase regulatory gene deficiency, etc. may be corrected by introduction of a wild-type gene into the haematopoietic stem cells, either by homologous or random recombination.

Other indications of gene therapy are introduction of drug resistance genes to enable normal stem cells to have an advantage and be subject to selective pressure during chemotherapy. Suitable drug resistance genes include, but are not limited to, the gene encoding the multi-drug resistance (MDR) protein.

Diseases other than those associated with hematopoietic cells can also be treated by genetic modification, where the disease is related to the lack of a particular secreted product including, but not limited to, hormones, enzymes, interferons, growth factors, or the like. By employing an appropriate regulatory initiation region, inducible production of the deficient protein can be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

In an additional aspect, the present invention is directed to various methods of utilizing human mesenchymal stem cells identified and isolated or enriched by the methods of the present invention for therapeutic and/or diagnostic purposes. For example, human mesenchymal stem cells find use in: (1) regenerating mesenchymal tissues which have been damaged through acute injury, abnormal genetic expression or acquired disease; (2) treating a host with damaged mesenchymal tissue by removal of small aliquots of bone marrow, isolation of their mesenchymal stem cells and treatment of damaged tissue with MSCs combined with a biocompatible carrier suitable for delivering MSCs to the damaged tissues site(s); (3) producing various mesenchymal tissues; (4) detecting and evaluating growth factors relevant to MSC self-regeneration and differentiation into committed mesenchymal lineages; (5) detecting and evaluating inhibitory factors which modulate MSC commitment and differentiation into specific mesenchymal lineages: and (6) developing mesenchymal cell lineages and assaying for factors associated with mesenchymal tissue development.

The present invention is also directed to methods of utilizing the mesenchymal stem cells for correcting or modifying connective tissue disorders, such as the regeneration of missing or damaged skeletal tissue, enhancing the implantation of various plastic or metal prosthetic devices through the attachment of the isolated mesenchymal stem cells onto the porous surfaces of the prosthetic devices or various tri-calcium or hydroxyapatite ceramic vehicles or carriers, which, upon the activation and subsequent differentiation of the mesenchymal stem cells, produce natural osSEQus or viscous bridges.

In addition, the present invention relates to various methods directed to using composite grafts of mesenchymal stem cells to augment the rate of hemopoietic cell reserve during bone marrow transplantation. An additional embodiment of the invention concerns various methods for using composite grafts of mesenchymal stem cells and ceramics implanted into hosts, such as into subcutaneous sites in nude mice, as catalysts for the production of a reservoir of hemopoietic stem cells.

In another aspect, the present invention relates to a method for repairing connective tissue damage. The method comprises the steps of applying a mesenchymal stem or progenitor cell-containing extract to an area of connective tissue damage under conditions suitable for differentiating the cells into the type of connective tissue necessary for repair.

Compositions according to the present invention which contain mesenchymal stem cells are especially useful for facilitating repair, reconstruction and/or regeneration of a connective tissue defect. Connective tissue, as used herein, includes bone, cartilage, ligament, tendon, stroma and muscle. Connective tissue defects include any damage or irregularity compared to normal connective tissue which may occur due to trauma, disease, age, birth defect, surgical intervention, etc. As used herein, connective tissue defects also refer to non-damaged areas in which cosmetic augmentation is solely desired. The methods and materials disclosed herein are especially suitable for use in orthopedic, dental, oral maxillofacial, periodontal, and other surgical procedures.

Although in a preferred embodiment, the mesenchymal stem cells are culturally expanded prior to use, it is also possible to use such mesenchymal stem cells without culture expansion. For example, mesenchymal stem cells may be derived from bone marrow and used after separation of blood cells therefrom, without expansion. Thus, for example, during a surgical procedure for repairing connective tissue using mesenchymal stem cells, bone marrow may be obtained from a patient, enriched in human mesenchymal stem cells, by removal of blood cells and isolation using ACE antibody and reintroduced to the patient during the procedure. The marrow-derived cells containing mesenchymal stem cells which are essentially free of blood cells may then be used to repair the patient's connective tissue.

Various vehicles may be employed for delivery of human mesenchymal stem cells for repair of connective tissue. The compositions may be designed as a patch for the damaged tissue to provide bulk and scaffolding for new bone or cartilage formation. The various compositions, methods, and materials described herein can, in accordance with the present invention, be used to stimulate repair of fresh fractures, non-union fractures and to promote spinal fusion. Likewise, repair of cartilage and other musculoskeletal tissues can be accomplished. In the case of spinal fusion, such compositions, methods, and materials can be used posteriorly with or without instrumentation to promote mass fusion along the lamina and transverse processes and anteriorly, used to fill a fusion cage to promote interbody fusion.

Keratinocytes isolated in the present invention may also be used for culture ex-vivo for use in treating burns; vehicles for gene therapy for systemic delivery of therapeutic agents such as but not limited to insulin, leptin or they may be used as a source of stem cells which may be reprogrammed into other tissues for therapeutic applications.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia before the priority date of each claim of this application.

Examples of the procedures used in the present invention will now be more fully described. It should be understood, however, that the following description is illustrative only and should not be taken in any way as a restriction on the generality of the invention described above.

EXAMPLES

Example 1

Isolation and Characterisation of BB9 Antibody (a) Isolation of Cells from Bone Marrow and Peripheral Blood Bone marrow was aspirated into preservative-free heparin from the sternum and posterior iliac crest of healthy volunteers after informed consent was obtained, according to procedures approved by the Human Ethics Committee of the Royal Adelaide Hospital. Bone marrow mononuclear cells (BMMNC) were isolated following centrifugation at 400 g over Ficoll (Lymphoprep, 1.077 g/dL; Nycomed Pharma AS, Oslo, Norway) and washed twice by centrifugation at 4° C. in HHF (Hank's Balanced Salt Solution (HBSS; Gibco/BRL, Glen Waverley, Victoria, Australia) supplemented with 20 mmol/L HEPES, pH 7.35, and 5% fetal calf serum (FCS; PA Biologicals, Sydney, NSW, Australia).

Mobilized peripheral blood (PB) was harvested and cryopreserved as previously described [17]. Cells were stored in liquid nitrogen until use. On the day of immunolabeling and cell sorting, ampoules of cells were thawed quickly at 37° C. As soon as the cells had thawed they were transferred into a round-bottomed tube (Falcon 2059; Becton Dickinson, Lincoln Park, N.J.) containing 10 mL thaw solution (HBSS supplemented with 2% BSA, 10 mM acid citrate and 50 kunitz units/mL DNAse). Cells were allowed to sit at room temperature for 10 minutes and were then centrifuged and washed twice in HHF. In order to remove any nonviable material, cells were isolated following centrifugation over Ficoll as described above. Cells from 2 cohorts of patients were used in this study, those mobilized with high dose cyclophosphamide (HDC) at a dose of 7 mg/m$^2$ plus G-CSF (5 µg/kg daily subcutaneously (sc) from day 2 until completion of apheresis) and with HDC plus GM-CSF (also 5 µg/kg/day sc from day 2 until completion of apheresis) [18].

Peripheral blood leukocytes (PBL) were isolated from normal donor PB drawn into preservative-free heparin. Briefly, pre-warmed Pentaspan (The Boots Co., Wellington, NZ) was added to PB at a ratio of 6.6 mL Pentaspan to 10 mL PB. These were mixed by inversion and incubated at 37° C. for 30 minutes. During the incubation the red cells sedimented and the upper layer containing PBLs was harvested. Cells from this layer were centrifuged and washed twice in HHF. These cells were then separated into mononuclear cells and granulocytes using a Ficoll technique similar to the one described above. The granulocytes and contaminating erythrocytes were pelleted through the Ficoll and, following removal of contaminating red cells by hypotonic lysis in 0.83% ammonium chloride, the leukocytes prepared in this manner routinely comprised >95% neutrophil granulocytes.

(b) Culture of Human Hematopoietic Cell Lines

Jurkat, Hut 78, CEM VLB-100 and Molt-4 (all T cell lines), HL60 (promyelocytic leukaemia), K562 (erythroleukaemic), Meg-01 (megakaryocyte), Hi Meg (megakaryocyte/leukaemia), Nalm-6 (B cell line), KG1 (myeloblastic leukaemic cell line), KG1a (myeloblastic), U937 (myeloid), HEL-DR$^+$ (erythroleukaemic), and RC2A (AML) cells were all grown in RPMI-1640 medium (Gibco/BRL, Glen Waverley, Victoria, Australia) supplemented with 10% FCS, penicillin (final concentration of 100 i.u./mL), gentamycin sulphate (100 µg/mL final) and 2 mM glutamine. UT7 (megakaryocytic/erythroleukaemic) and TF-1 cells were grown in RPMI-1640 with 10% FCS with penicillin, gentamycin and glutamine as above and 2 ng/mL GM-CSF (generously donated by Amgen, Thousand Oaks, Calif.). M07e cells were grown in Alpha MEM (Alpha Modification of Eagles medium) supplemented with 10% FCS with penicillin, gentamycin and glutamine as above and 5 ng/mL IL-3 (Amgen, Thousand Oaks, Calif.).

(c) Culture of Non-Hematopoietic Human Cell Lines

HFF2 (fibroblast cells) and MCF-7 (breast cell carcinoma) were grown in DMEM (Gibco/BRL) supplemented with 10% FCS, penicillin, gentamycin sulphate and glutamine. MG63 (osteosarcoma cells) were grown in Alpha MEM (Gibco/BRL) supplemented with 10% FCS with penicillin, gentamycin and glutamine as above.

(d) Bone Marrow Stromal Cells

Bone marrow stromal cells used for immunization were isolated from human STRO-1$^+$ BMMNC purified by FACS as previously described [19]. These cells were cultured in Alpha medium supplemented with 20% FCS, penicillin (100 i.u./mL), streptomycin sulphate (100 µg/mL) and glutamine (2 mM) and with a long lived derivative of L-ascorbate, ascorbic acid 2-phosphate (ASC-2P, Sigma, St Louis, Mich., USA). Cells were cultured at 37° C. 5% CO$_2$ in a humidified incubator for several weeks with weekly medium changes.

(e) Monoclonal Antibody Generation

Antibody BB9 was developed following immunization of a BALB/c mouse with a series of independently derived human bone marrow stromal cells designated HPV/MSC resulting from infection of STRO-1$^+$ stromal cells with an amphotropic retrovirus containing human papilloma virus (HPV) 16 E6/E7 open reading frame (HPV16 E6/E7orf) [20-22]. Briefly, BALB/c mice were immunized intra-peritoneally (IP) with between 2 and 10×10$^6$ cells of the HPV/MSC cells in PBS containing 50 µg muramyl dipeptide (Sigma) as adjuvant. Mice were boosted twice with the same dose of cells given IP at three weekly intervals and 4 days prior to fusion with 10$^6$ cells administered intravenously. Splenocytes isolated from immunized mice were then fused with the NS-1 murine myeloma cell line according to standard methods [23] and the resulting hybridomas selected in medium containing HAT [24].

Hybridomas arising from the fusion were initially screened for production of antibodies reactive with HPV/MSC stromal cells. This was performed by means of an indirect immunofluorescence assay on fresh, unfixed stromal cells grown in 96 well plates. Antibodies reactive with this stromal cell line were then subjected to a negative screen in order to eliminate antibodies reactive with PBL. This was performed by staining PBL sequentially with the hybridoma supernatants and fluorescein isothiocyanate (FITC)-conjugated-F(ab)$_2$ sheep anti-mouse immunoglobulin (Ig) (DDAF reagent: Silenus, Melbourne, Australia). Staining was performed in round-bottom 96-well plates (Nunc A/S, Kamstrup, Denmark) and washing after each incubation step was achieved by adding cold HHF followed by centrifugation. After the final wash the PBL were transferred to flat bottom 96 well plates previously coated (30 minutes at room temperature) with poly-L-lysine (diluted 1 in 10; Sigma) and again centrifuged in order to promote cell attachment. After removal of the excess HHF the cells were fixed in-situ by the addition of 100 µl of FACS fix (1% formalin, 2% glucose and 0.02% sodium azide in PBS) and subsequently scored visually for antibody reactivity by examination under a fluorescence microscope (Olympus BH2-RFCA, Olympus Optical Co. Ltd. Tokyo, Japan). Antibodies that were non-reactive with PBL were then examined for their binding to BMMNC by means of flow cytometric analysis performed as described below. Antibody BB9 was selected initially based upon its reactivity with a minor subpopulation of lymphoblastoid cells and in subsequent assays, according to its binding to a subpopulation of CD34$^+$ cells. Following its identification, the BB9 hybridoma was cloned three times by limiting dilution and the isotype of the antibody determined using a commercial kit (Böehringer Mannheim, Castle Hill, NSW, Australia). BB9 was shown to be of the IgG$_1$ isotype. All subsequent studies were performed with purified BB9 antibody isolated from spent tissue culture supernatant using Protein A-Sepharose (Pharmacia, North Ryde, NSW, Australia) according to the manufacturers recommendations. Attempts to conjugate BB9 under standard conditions with amine reactive derivatives of Fluorescein Isothiocyanate (FITC) or biotin resulted in loss of binding activity of the antibody. Consequently, all analysis of the pattern of binding of BB9 to primary hematopoietic cells and to cell lines representative of various hematopoietic lineages were performed by means of indirect immunofluoresence staining.

(f) Immunolabeling of Hematopoietic Cells for Flow Cytometric Analysis and Fluorescence-Activated Cell Sorting (FACS)

Prior to immunolabeling, primary hematopoietic cells (BMMNC, PBMNC, PBL) or hematopoietic cell lines were incubated in HHF supplemented with 4% normal human serum (Red Cross, Adelaide, South Australia; HHF-NHS) for 30 minutes on ice to block Fc receptors. Cells were then labeled either with the individual antibodies or simultaneously with a combination of the anti-CD34 MAb 43A1 (mouse IgG$_3$; a generous gift from Dr. H.-J. Bühring, Tübingen University) [25] and antibody BB9 (mouse IgG$_1$) both diluted to a final concentration of 20 µg/mL in HHF. Additional samples were stained in parallel with isotype-matched, non-binding control IgG$_3$ (Southern Biotechnology Associates, Birmingham, Ala.) or IgG$_1$ (MAb 1B5, anti-Giardia, generously provided by Dr Graham Mayerhofer, Department of Microbiology, University of Adelaide) antibodies either alone or in various pairwise combinations with the 43A1 and BB9 antibodies as appropriate. All antibody incubations were performed for 45 minutes on ice and were followed in all cases by two washes in an excess of HHF at 4° C. Specifically bound monoclonal antibody was then revealed by incubation with a combination of optimally titred isotype-specific goat antibodies directed against mouse-IgG$_1$ (conjugated to Phycoerythrin, PE) and mouse-IgG$_3$ (conjugated to FITC; both from Caltag; San Francisco, Calif.). After a further two washes in HHF the cells were suspended at approximately 10$^7$/mL in either FACS-FIX (for flow cytometric analysis) or cold HHF for FACS.

Three-colour flow cytometric analysis was performed to examine expression of the antigen identified by BB9 on defined subpopulations of CD34$^+$ BM cells. The majority of these analyses were performed using unfractionated BMMNC while some were performed with CD34$^+$ cells pre-enriched by 561-Dynabeads (Dynal, Oslo) as described previously [26]. Additional studies were performed with BMMNC to examine the retention of the supravital fluorescent dye Rhodamine 123 (Rh123) by CD34$^+$ cells fractionated according to BB9 expression. Cells were first incubated for 45 minutes at 37° C. in HHF supplemented with Rh123 (Molecular Probes Inc, Oregon) at a final concentration of 0.1 µg/mL. After two washes in cold HHF, the cells were incubated in HHF for a further 15 minutes at 37° C. to allow efflux of unbound Rh123 and then washed in cold HHF-NHS. Immunostaining was then performed using 43A1 and BB9 as described above, with the exception that 43A1 was detected by means of sequential incubation with biotinylated goat anti-mouse IgG$_3$-specific antibody and streptavidin-Tricolour (SAV-TC; both from Caltag). Co-distribution of CD34/CD38/BB9 and CD34/CD90/BB9 was assessed by firstly incubating cells with 43A1 and BB9 followed by anti-mouse IgG$_3$-FITC and anti-mouse IgG$_1$-Tricolour (TC) (both from Caltag) as above. Cells were then incubated with an excess of ascites containing a non-binding mouse IgG$_1$ antibody, 3D3 [27] in order to block excess sites on the anti-mouse IgG$_1$-TC after which was added either Leu17-PE (CD38, IgG$_1$; Becton Dickinson, Mountain View, Calif.) or PR13$_{BIOTIN}$ (IgG$_1$ anti-CD90; a generous gift from Drs. Beth Hill and Ben Chen, Systemix Inc., Palo Alto, Calif.) for a further 45 minutes. Bound PR13$_{BIOTIN}$ was localised by a final incubation with SAV-PE (Caltag). An aliquot of cells was also stained in parallel with IgG$_1$-PE or IgG$_1$-$_{BIOTIN}$ (Becton Dickinson) in order to assess the effectiveness of the blocking step. Cell cycle analysis of BMMNC was performed by initially labeling cells with 43A1 and BB9 then subsequent incubation with biotinylated goat anti-mouse IgG$_3$-specific antibody and SAV-TC and PE-conjugated goat anti-mouse IgG$_1$ as described above. Cells were then blocked with an excess of irrelevant mouse IgG$_1$ ascites for 30 minutes, washed twice in HHF, twice in PBS and permeabilised with ice cold 70% ethanol for 10 minutes. Cells were washed twice in PBS and blocked for a further 30 minutes with 3% goat serum in PBS. FITC-conjugated Ki67 MAb (Immunotech, Marseille, France) or IgG$_1$-FITC control was added to the cell suspension at a final dilution of 1 in 10 and cells were incubated on ice for 45 minutes.

Flow cytometric analysis was performed using a Profile II or EPICS XL-MCL flow cytometer (Coulter Corp., Hialeah, Fla.). Twenty thousand events were collected per sample as list mode data and analysed using Coulter ELITE software. Cell sorting was performed using a FACStar$^{PLUS}$ cell sorter (Becton Dickinson) equipped with an argon laser emitting 488 nm light at 200-250 mW. Sorting was restricted to those cells which, based on their light scattering properties, fell within a defined lymphocyte/blast window [4]. Thresholds for the selection of sort gates was based on the levels of staining obtained with the isotype control antibodies. Cells were collected into tubes containing Iscove's Modified Dulbecco's Medium (IMDM; Gibco/BRL) supplemented with 5% FCS. Purity of the selected populations was assessed by analysis of an aliquot of sorted cells and was routinely greater than 98%.

(g) Staining of BM Stromal Cells with BB9 Antibody

Bone marrow stromal cells derived as described above were stained in situ with BB9 MAb. Cells were grown in glass 8-well chamber slides (Nunc) overnight at 37° C. prior to staining. The cells were stained with BB9 or IgG$_1$ isotype control antibody 1B5 (both at final concentrations of 20 μg/mL in HHF) on ice for 45 minutes and washed twice with HHF. Specifically bound antibody was revealed using FITC conjugated anti-mouse-IgG$_1$ monoclonal antibody (Caltag) at a dilution of 1 in 50 in HHF for 30 minutes on ice in the dark. After two final washes cells were fixed with FACS fix and observed using a fluorescence microscope (Olympus BH2-RFCA).

(h) Purification of BB9$^+$ Cells from BMMNC using Magnetic-Activated Cell Sorting (MACS)

In order to assess the expression of lineage-specific antigens co-expressed with BB9 antigen, BB9$^+$ BMMNC were isolated by means of magnetic-activated cell sorting (MACS) [28]. Briefly, BMMNC (0.5-1×10$^8$ cells) were suspended in 0.5 mL BB9 antibody (20 μg/mL final concentration) for 45 minutes on ice. The cells were then washed twice in HHF and resuspended in 0.5 mL HHF containing a 1/50 dilution of biotinylated goat anti-mouse IgG$_1$ (Caltag) for 30 minutes at 4° C. The cells were washed three times in MACS buffer (comprising single strength Ca$^{2+}$- and Mn$^{2+}$-free phosphate buffered saline (PBS) supplemented with 1% BSA, 5 mmol/L EDTA and 0.01% sodium azide) and resuspended in 900 μL MACS buffer to which 100 μL of streptavidin microbeads (Miltenyi Biotec, Bergisch Gladbach, Germany) was added. After incubating for 30 minutes at 4° C., SAV-PE conjugate (1/50; Caltag) was added for an additional 15 minutes. Cells were washed twice in MACS buffer and a small aliquot removed for flow cytometric analysis. The remaining cells were separated on a magnetic stainless steel wool column (column capacity 10$^8$ cells; Miltenyi Biotec) according to manufacturer's recommendations. The BB9$^-$ cells were collected as column eluate, while the BB9$^+$ cells remained attached to the magnetized matrix. To obtain the BB9$^+$ cells, the column was removed from the magnet and then flushed with MACS buffer into another tube. Small samples were taken from each of the BB9$^+$ and BB9$^-$ cell populations for cytometric analysis to examine the recovery and purity of cells in each fraction.

The BB9$^+$ cells obtained from the MACS column were then incubated with an excess of ascites containing a non-binding mouse IgG$_1$ antibody as described above. Cells were then stained by the addition of the FITC conjugated lineage markers as follows: IgG$_1$ FITC (Dako A/S, Glostrup, Denmark), CD7 FITC (BDIS), CD3 FITC (BDIS), CD10 FITC (Dako), CD19 FITC (Immunotech), CD33 FITC (Coulter), CD14 FITC (Dako), CD15 FITC (Immunotech), CD34 FITC (BDIS), CD61 FITC (BDIS), Glycophorin A FITC (Dako) and CD71 FITC (BDIS) for 45 minutes at 4° C. Cells were washed twice in HHF and fixed in FACS fix and flow cytometric analysis was performed using an EPICS XL-MCL flow cytometer (Coulter Corp., Hialeah, Fla.). Twenty thousand events were collected per sample as list mode data and analysed using Coulter ELITE software.

(i) Hematopoietic Progenitor Cell Clonogenic Assays

Granulocyte-macrophage colony-forming cells (CFU-GM), erythroid progenitors (BFU-E), and multipotent colony-forming cells (CFU-Mix) were assayed as previously described [29]. Briefly, triplicate 1 mL cultures were established in 35 mm dishes in IMDM supplemented with 0.9% methylcellulose, 30% FCS, 1% BSA (Fraction V; Sigma), 3 mmol/L L-glutamine, and 5×10$^{-5}$ mmol/L 2-mercaptoethanol. Colony growth was stimulated by the addition of 10 ng of each of the recombinant human interleukin-3 (IL-3), IL-6, granulocyte-macrophage colony-stimulating factor (GM-CSF), granulocyte-colony-stimulating factor (G-CSF), stem cell factor (SCF) (all factors were generously provided by Genetics Institute, Boston, Mass. and Amgen, Thousand Oaks, Calif.) and 4U of erythropoietin (Eprex; Janssen Cilag, Auckland, New Zealand). CFU-GM, BFU-E and CFU-Mix were enumerated on day 14 according to standard criteria. All cultures were established in triplicate by plating 500 cells per dish.

(j) Pre-CFU Culture

This is a stroma-free, cytokine-dependent suspension culture system previously reported by this laboratory [29], which measures the de novo generation of CFU-GM as an index of precursors (pre-CFU) of CFU-GM. Assays were established in triplicate 1 mL cultures in 24 well plates with 10$^3$ CD34$^+$, CD34$^+$BB9$^+$ and CD34$^+$BB9$^-$ cells isolated by FACS from either BM or mobilised PB. Each 1 mL culture comprised IMDM, 30% FCS, 1% BSA, 3 mmol/L L-glutamine, 5×10$^{-5}$ mol/L 2-mercaptoethanol and was supplemented with the following recombinant growth factors: IL-3 (10 ng/mL), IL-6 (20 ng/mL), G-CSF and SCF (each at 100 ng/mL). Additional factors were added to the same final concentration on day 7, and on days 14, 21, 28, 35 and 42 the cultures were split 1 in 10 into fresh medium containing growth factors. CFU-GM present after 14, 21, 28, 35 and 42 days of culture were enumerated as described above and the cumulative number of cells and CFU-GM at any given time point were calculated by taking into account the cumulative dilution factor for the culture over the entire culture period.

(k) Protease Sensitivity of the BB9 Antigen

To investigate the nature of the antigen recognized by BB9, human hematopoietic cell lines found to bind BB9 were treated in vitro with a variety of proteases in order to identify those that resulted in loss of antibody binding. Prior to enzyme treatment the cells were washed in HBSS (in the absence of serum) and then incubated at 10$^6$ cells/mL for 1 hour at 37° C. in the same medium containing the following proteases: bromelain, chymotrypsin, papain, pepsin, pronase, thermolysin and trypsin at a final concentration of 20 µg/mL, chymopapain at 100 U/mL, dispase at 4 mg/mL and proteinase K at 1 µg/mL. All enzymes were obtained from Boehringer Mannheim (Mannheim, Germany) with the exception of papain (Sigma) and chymopapain (Boots, Poole, UK). After protease treatment, cells were washed twice in HHF and assayed for expression of BB9 antigen using immunofluorescence analysis as described above. Chymopapain treatment of UT7 cells was repeated using a variety of control antibodies including anti-CD71 (Becton Dickinson) and 9B3 (anti-MHC Class I antibody) to assess the specific nature of the antigen release.

(I) Immunoprecipitation Analysis

UT7 cells were washed twice in phosphate buffered saline (PBS) and resuspended at $2 \times 10^8$ cells per mL in the same buffer. Cells were surface labeled with 2 mCi $^{125}$I, using lactoperoxidase as catalyst [30] for 15 minutes at room temperature and then washed four times in PBS. UT7 cells were lysed at a final concentration of $2 \times 10^7$ cells per mL with 1% CHAPS detergent (Sigma) in 140 mM NaCl, 0.5 mM $MgCl_2$, 0.5 mM $CaCl_2$, 10 mM Tris, pH 7.4 (CHAPS buffer) containing the protease inhibitors PMSF (phenyl methyl sulfonyl fluoride), TPCK (L-(tosylamido-2-phenyl) ethyl chloromethylketone), TLCK (1-Chloro-3-tosylamido-7-amino-L-2-heptanone) and NPGB (p-Nitrophenyl-p'-guanidino-benzoate-HCl) (all purchased from Sigma) for 30 minutes on ice. Nuclei and non-solubilized cellular matter were pelleted by centrifugation at 18,000 g for 20 minutes and lysate was precleared overnight with sheep anti-mouse Ig Dynabeads (Dynal). 1.5 mL of lysate was used for each immunoprecipitation using 1B5 (isotype-matched negative control) and BB9. Antibodies were prebound to M450 Rat anti-mouse $IgG_1$ Dynabeads overnight using 50 µg antibody with 50 µL ($2 \times 10^7$) beads in 1 mL PBS/0.1% BSA. Beads were washed ×2 with PBS/BSA and ×1 with CHAPS buffer before addition to the cell lysate. Cell lysate and beads were rotated for 2-3 hours at 4° C. and then beads were removed using a Dynal MPC-6 magnet, washed ×3 with CHAPS buffer, boiled for 5 minutes in gel sample buffer (0.0625 M Tris pH 6.8, 10% glycerol, 20% SDS and 0.00125% bromophenol blue) and run on 4-20% gradient SDS-PAGE. Gels were run overnight at 8-10 mA, fixed for 30 minutes in methanol:acetic acid:water (5:1:4) dried under vacuum and assessed by phosphorimage analysis (Molecular Dynamics Inc, Sunnyvale, Calif.) or autoradiography at −70° C.

1. Monoclonal Antibody (MAb) BB9 Binds to a Minor Subpopulation of CD34+ BMMNC

The murine monoclonal antibody BB9 was generated following immunization with human BM derived stromal cells and was identified in the initial hybridoma screening based upon its reactivity with the immunogen and lack of significant binding to PBMC. Examination of immunolabelled stromal cells by fluorescent microscopy revealed a delicate punctate pattern of BB9 expression, which appeared to be restricted to the cell surface. Flow cytometric analysis confirmed the very low level reactivity with PBMC but demonstrated binding of BB9 to a minor subpopulation (average 9.9±2.2%; n=10) of cells in adult human BM characterized by low forward and low perpendicular light scatter properties (FIG. 1A). Subsequent two-colour immunofluorescence analysis of mononuclear cells from adult bone marrow with BB9 and anti-CD34 antibody revealed binding of BB9 to a subpopulation of CD34+ cells (mean 22.4; range 8.3-40.8%, n=10). Significantly, the intensity of BB9 staining was greatest on cells exhibiting the highest CD34 antigen density (FIG. 1B). In addition, although a small proportion of CD34− cells expressed BB9, the intensity of BB9 staining on these cells was consistently less than that expressed by CD34+ cells.

To determine the identity of other (CD34−) cells, which also bound BB9, BB9+ cells were isolated from BMMNC by means of magnetic activated cell sorting (MACS) and then stained with each of a panel of MAbs specific for particular hematopoietic lineages. As shown in Table 1, approximately one third (39.8%±20.5%; n=3) of BMMNC identified by BB9 are B-lymphocytes as demonstrated by their expression of CD19. A significant proportion of BB9+ cells also co-expressed the T-lymphoid antigen CD7 (18.8%±7.6%; n=3), the myeloid marker CD33 (10.6±6.1%; n=3) and a further 11.7% of cells also stained with anti-CD71 antibody. Lower proportions (between 1-6% of cells) co-expressed CD3, CD14, CD61, and glycophorin A.

TABLE 1 shows Lineage Antigens expressed by BB9+ BMMNC.

| Lineage Marker | mean ± SEM |
| --- | --- |
| CD7 | 18.8 ± 7.6 |
| CD3 | 5.7 ± 2.8 |
| CD19 | 39.8 ± 20.5 |
| CD33 | 10.6 ± 6.1 |
| CD14 | 1.3 ± 0.3 |
| CD34 | 9.8 ± 7.7 |
| CD61 | 2.0 ± 1.0 |
| Glycophorin A | 2.0 ± 0.2 |
| CD71 | 11.7 ± 7.1 |

BB9+ cells were purified from BMMNC using MACS as described. Cells were stained to detect BB9 using anti-mouse $IgG_1$-biotin and SAV-PE, and other lineage antigens with antibodies directly conjugated to FITC. The co-expression of these markers with BB9 was visualised using analysis with Coulter Elite software. 20,000 events were analysed for each sample. Data represent the proportion of BB9+ cells (%, mean±SEM of three independent BM samples) that co-express the respective lineage antigens.

To investigate the nature of the CD34+ cells identified by BB9, two colour FACS was employed to isolate CD34+BB9+ and CD34+BB9− subpopulations according to the sort regions shown in FIG. 2. Each subpopulation was assayed for content of clonogenic hematopoietic progenitor cells in standard semi-solid cultures. Data from 8 experiments (summarized in Table 2) demonstrate that myeloid progenitors (CFU-GM) are present in both CD34+BB9+ and CD34+BB9− subpopulations. No significant differences (p=0.63) in the incidence of CFU-GM was evident between these two subpopulations or between either subpopulation and unfractionated CD34+ cells (CD34+ versus CD34+BB9+ p=0.44; CD34+ versus CD34+BB9− p=0.87). Similarly, erythroid progenitors (BFU-E) were also detected in both subpopulations although there was a relative depletion in the incidence BFU-E within the CD34+BB9+ fraction as compared to either total CD34+ cells (p=0.03, paired t-test) or the CD34+BB9− fraction (p=0.01).

TABLE 2 shows Incidence of clonogenic progenitors within CD34+, CD34+BB9+ and CD34+BB9− cell fractions.

| Cell Source | Cell Type | CFU-GM | BFU-E | CFU-Mix |
| --- | --- | --- | --- | --- |
| Bone | CD34+ | 232.1 ± 67.6 | 81.5 ± 39.2 | 4.5 ± 3.2 |
| Marrow | CD34+BB9+ | 277.1 ± 114.1 | 38.7 ± 33.6 | 3.7 ± 5.1 |
| (n = 8) | CD34+BB9− | 239.0 ± 137.7 | 88.1 ± 25.3 | 4.2 ± 2.8 |

TABLE 2-continued shows Incidence of clonogenic progenitors within CD34+, CD34+BB9+ and CD34+BB9− cell fractions.

| Cell Source | Cell Type | CFU-GM | BFU-E | CFU-Mix |
|---|---|---|---|---|
| Mobilized | CD34+ | 198.0 ± 119.1 | 185.7 ± 96.8 | 2.2 ± 0.9 |
| Blood | CD34+BB9+ | 198.8 ± 142.1 | 89.5 ± 53.2 | 1.0 ± 1.1 |
| (n = 6) | CD34+BB9− | 142.8 ± 69.1 | 245.8 ± 151.7 | 1.3 ± 2.4 |

CD34+ cells from normal bone marrow donors (n=8) or mobilised peripheral blood samples (n=6, 3 from HDC+G-CSF and 3 from HDC+GM-CSF) were separated into BB9+ and BB9− subfractions. Cells were plated in methylcellulose cultures containing IL-3, IL-6, G-CSF, GM-CSF, SCF and Epo for 14 days at 37° C./5% $CO_2$. Colonies were identified in situ and their types are abbreviated as follows: CFU-GM=granulocyte and/or macrophage; BFU-E=erythroid; CFU-Mix=mixed colonies containing erythroid and myeloid cells and/or megakaryocyte. The numerical data represents the mean (±Standard Deviation) of colonies per 1000 cells of each phenotype plated.

Multipotential progenitors (CFU-Mix) were also identified in both CD34+BB9+ and CD34+BB9− fractions but no consistent trend was observed in their incidence in either subpopulation (Table 2). Correcting for the incidence of the BB9+ and BB9− subpopulations within the CD34+ population, the recovery of CFU-GM, BFU-E and CFU-Mix in the CD34+BB9+ subpopulation was 33.8±6.2%, 13.8±3.9% and 24.5±12.8%, respectively.

2. Hierarchically Primitive HPC Express the Antigen Identified by BB9

In order to investigate the expression of BB9 on hierarchically primitive HSC a series of 3-colour immunolabeling procedures were performed. As shown in panel B of FIG. 2, expression of the BB9 antigen is inversely correlated with that of CD38, the highest levels being found on CD34+ CD38− cells and the lowest on the CD34+ CD38+ population. In addition, as shown in panel C of FIG. 2, binding of BB9 co-distributes to a significant extent with that of CD90 (Thy-1); CD34+ CD90+ representing a phenotype previously shown to contain the majority of LTC-IC and cells with the capacity to engraft in lethally irradiated immunodeficient mice [7]. CD34+ cells with low Rh123 retention (CD34+ Rh123$^{dull}$) are virtually all BB9+ and, moreover, demonstrate markedly higher levels of BB9 antigen expression than those exhibited by CD34+Rh123$^{bright}$ cells (FIG. 2, panel A). To investigate the cell cycle status of CD34+ cells co-expressing BB9 antigen, 3-colour flow cytometric analysis of BMMNC was performed in combination with Ki67 MAb. Ki67 detects a nuclear antigen present only in proliferating cells at $G_1$, S, $G_2$ and M phases of the cell cycle but not in $G_0$ [31]. As shown in FIG. 3A, Ki67 binds to approximately 55% of CD34+ cells. The remainder of CD34+ cells which fail to bind Ki67 (region R1 of FIG. 3A) are defined as $G_0$ cells. Analysis of listmode data files enabled examination of the pattern of BB9 expression on CD34+Ki67+ cells (within R2) and CD34+Ki67− cells (within R1). Panel B of FIG. 3 demonstrates that non-proliferating hematopoietic progenitor cells (CD34+Ki67−; within R1 of FIG. 3A) exhibit the highest level of BB9 expression, with 79% considered BB9+. In contrast, proliferating cells (Ki67+, within R2 of FIG. 3A) exhibit low-level expression of BB9 (FIG. 3C).

Collectively, therefore, these data demonstrate that CD34+BB9+ cells exhibit a number of phenotypic characteristics previously ascribed to primitive human HPC. To further investigate the expression of the BB9 antigen on hierarchically primitive HPC (pre-CFU), CD34+BB9+ and CD34+BB9− BMMNC subpopulations were assayed for their capacity to initiate and sustain hematopoiesis in stroma-free, cytokine dependent suspension as described previously [29]. Sorted fractions were cultured in a combination of IL-3, IL-6, G-CSF and SCF (36GS) [29] and assayed at weekly intervals over a period of 6 weeks for their production of CFU-GM and mature myeloid cells. FIG. 4 is a summary of data from 10 experiments. The production of CFU-GM (panel A) was significantly greater from the CD34+BB9+ than from the CD34+BB9− subpopulation at all time points measured (p values range from 0.0004 to 0.008) with the exception of day 35. At the cessation of cultures (day 42) the mean number of CFU-GM generated from $10^3$ CD34+BB9+ cells was $2.2 \times 10^{5 \pm 1.2 \times 10^5}$ while the same number of CD34+BB9− cells produced only a mean of 7812 colonies. In accord with this, the corresponding production of maturing myeloid cells was greater from the BB9+ subpopulation at all time points (p values from 0.027 to 0.55) leading to the generation of a mean of $2.5 \times 10^8$ cells at day 42 (FIG. 4B) These data therefore demonstrate that primitive HPC with the capacity to initiate and sustain hematopoiesis under these culture conditions are restricted to a subpopulation of CD34+ cells identified by MAb BB9.

3. The Antigen Identified by BB9 is Expressed at High Levels by CD34+ Cells in Mobilized Peripheral Blood The pattern of BB9 binding to CD34+ cells was analyzed in steady state blood and mobilized peripheral blood (MPB). These studies were performed using samples obtained from normal donors or patients in which blood progenitor cell mobilization was induced following administration of either high dose cyclophosphamide (HDC) followed by G-CSF or with HDC plus GM-CSF. Analysis of steady state blood revealed that BB9 bound to approximately 5% of CD34+ cells (5.08%±0.58; n=4), a significantly lower proportion than previously observed for steady state BM CD34+ cells (p=0.026). In contrast, a consistently higher proportion of CD34+ cells in mobilized peripheral blood were found to bind BB9 (FIG. 5). A mean of 48.4%±4.3 (n=3) of CD34+ cells elicited by HDC+G-CSF and 54.7%±2.9 (n=3) of those mobilized by the combination of HDC+GM-CSF exhibited the BB9 antigen, approximately double the proportion observed in the CD34+ population isolated from steady state BM (see Table 3) and significantly, 4-5 fold more than present in steady state blood (p=0.0013). Moreover, the BB9 antigen density on both populations of mobilized CD34+ cells was higher than that on CD34+ cells in steady state peripheral blood.

TABLE 2 shows expression of BB9 on mobilized blood, normal adult bone marrow and steady state peripheral blood.

| Donor type (n) | Mononuclear cells expressing BB9 | BB9+ cells expressing CD34 | CD34+ cells expressing BB9+ |
|---|---|---|---|
| HDC + G-CSF (3) | 19.9 ± 3.5 | 15.3 ± 6.2 | 48.4 ± 4.3 |
| HDC + GM-CSF (3) | 28.0 ± 7.6 | 34.4 ± 9.7 | 54.7 ± 2.9 |
| Normal BM (10) | 9.9 ± 2.2 | 17.0 ± 4.3 | 22.4 ± 3.3 |
| Normal PB (4) | 4.7 ± 0.6 | 3.3 ± 2.0 | 5.1 ± 0.6 |

Samples were labeled with the anti-CD34 Mab 43A1 ($IgG_3$) and BB9 ($IgG_1$) or in parallel with isotype matched control Mab then visualized by aubsequent labeling with isotype-specific antibodies against mouse-$IgG_3$ (conjugated to FITC) and mouse $IgG_1$ (conjugated to PE). The data from at least 20,000 cells were acquired then analyzed using Coulter ELITE software. The data represents the proportion (%, mean±SEM) of cells expressing the indicated antigen from cells isolated from the respective donor sources (mobilization following high dose cyclophosphamide [HDC]+G-CSF or +GM-CSF; normal adult bone marrow; or steady state adult peripheral blood).

Clonogenic assays performed on CD34$^+$BB9$^+$ and CD34$^+$BB9$^-$ subpopulations isolated by FACS from each of the six mobilized blood samples demonstrated a qualitatively similar partitioning of CFU-GM and BFU-E into the BB9$^+$ and BB9$^-$ fractions to that found in BM (Table 2). CFU-GM were found at a similar incidence within both the CD34$^+$BB9$^+$ and CD34$^+$BB9$^-$ fractions. However, in accord with the BM samples, BFU-E were significantly depleted in the CD34$^+$BB9$^+$ cell fraction as compared to the CD34$^+$BB9$^-$ cell fraction (p=0.033). For the HDC+G-CSF samples, 49.4%±12.8 (range 25.8-70.0%) of CFU-GM and 21.3%±13.2 (range 0-45.4%) of BFU-E were recovered in the CD34$^+$BB9$^+$ subpopulation. Similarly, for the three HDC+GM-CSF samples, the CD34$^+$BB9$^+$ subpopulation contained a mean of 65.9%±1.9 (range 62.2-68.0%) of CFU-GM and 36.6%±9.3 (range 19.5-51.3%) of BFU-E.

As shown for the BM cells, pre-CFU assay of CD34$^+$BB9$^+$ and CD34$^+$BB9$^-$ cells isolated from MPB demonstrated greater generation of both CFU-GM (panel A, FIG. 6) and maturing myeloid cells (panel B, FIG. 6) from the BB9$^+$ than from the BB9$^-$ subpopulation at all time points measured. At the cessation of cultures (day 35) the mean number of CFU-GM generated from 10$^3$ CD34$^+$BB9$^+$ cells was 12,497±7,764 while the same number of CD34$^+$BB9$^-$ cells produced only 119±82 colonies. The corresponding production of maturing myeloid cells was greater from the CD34$^+$BB9$^+$ subpopulation at all time points leading to the generation of a mean of 7.5×10$^6$ cells at day 35 compared to 1.2×10$^6$ from CD34$^+$BB9$^-$ cells (FIG. 6). These data therefore demonstrate that in mobilised PB as in BM, the primitive HPC are restricted to a subpopulation of CD34$^+$ cells identified by MAb BB9.

4. BB9 Identifies a Chymopapain-Sensitive Glycoprotein of Molecular Weight 160 kDa.

The binding of BB9 to leukaemic cell lines representing a variety of hematopoietic lineages and other cell lines was also investigated. As shown (Table 3), BB9 bound at high levels to several cell lines including HL60, K562, Meg-01, UT7, MG63 and dermal fibroblast cells. Low to intermediate expression of the BB9 antigen was observed on the KG1, RC2A and MCF-7 cell lines and on the B cell line Nalm-6 while KG1a, MO7e and the T cell lines Jurkat, Hut 78, CEM VLB-100 and Molt-4 were all negative. Since the highest level of expression of the BB9 antigen was consistently observed on the GM-CSF-dependent UT7 cells, this line was used in all subsequent studies to investigate the nature of the antigen. To determine whether BB9 identified a protein epitope, UT7 cells were treated with a range of proteases in order to identify those which prevented subsequent binding of BB9 as assessed by flow cytometry. Bromelain, chymotrypsin, papain, pepsin, pronase, proteinase K, trypsin and thermolysin were all without effect in this assay but chymopapain completely abrogated specific labelling with BB9 as was also seen for CD71 which was used as a positive control in this assay (data not shown). In addition, treatment with PI-PLC while efficiently removing CD59 and CD90 from UT7 cells (data not shown) did not alter the binding of BB9 demonstrating that the BB9 epitope is not expressed on a GPI-linked glycoprotein. Finally, BB9 immunoprecipitated a glycoprotein from surface $^{125}$I-labelled UT7 cells with an apparent molecular weight under reducing conditions of 160 kDa (FIG. 7).

Although a wide variety of cell surface molecules have been identified on mature haemopoietic cells it has proven much more difficult to identify surface antigens that are restricted to hematopoietic stem and progenitor cells in human hematopoietic tissues. This may in part be due both to practical constraints such as the limited numbers of HPC available for immunization and screening but equally importantly to the well documented co-expression on both primitive and mature hematopoietic cells of a wide variety of surface antigens whose presence on the immunizing HPC population may consequently dominate the immune response rendering the identification of antigens restricted to HPC much more unlikely. In an attempt to circumvent these problems we chose to immunize mice with bone marrow stromal cells, a plentiful source of cells for immunization lacking many of the antigens shared with mature hematopoietic cells but which exhibit many of the cell surface antigens expressed on hematopoietic stem and progenitor cells including CD34 [12,13] CD90 [14], CD164 [15] and, in the mouse, Sca-1 [16]. We therefore hypothesized that immunization with bone marrow stromal cells may elicit antibodies to additional antigens co-expressed by these cells and primitive HPC and in fulfillment of this hypothesis we developed monoclonal antibody BB9.

We have shown that BB9 binds to approximately 10% of bone marrow mononuclear cells, 60% of which exhibit T or B-lymphocyte restricted antigens while approximately 20% co-express CD34. Although phenotypically diverse, the BB9$^+$ population as a whole is non-proliferating as demonstrated by low to undetectable levels of CD71 expression and lack of immunostaining with Ki67 which detects a nuclear antigen present only during the G$_1$, S, G$_2$ and M phases of cell cycle, not in G$_0$ [31]. Significantly, within the BM CD34$^+$ population only 20% of cells exhibit the BB9 antigen, but included within this subpopulation are the great majority of cells with candidate hematopoietic stem cell phenotype as identified by their lack of CD38 [6], low retention of Rh123 [32] and expression of CD90 [8]. In accord with these data, functional assays further demonstrated that primitive HPC with the capacity to initiate and sustain hematopoiesis in cytokine dependent, stromal cell-free culture were restricted to the CD34$^+$BB9$^+$ subpopulation. Similar observations were made with samples of blood stem cells mobilized by two different regimens suggesting that the specificity of BB9 for primitive HPC seen in BM also extends to mobilized peripheral blood. Of note, a significantly higher proportion of CD34$^+$ cells in MPB were BB9$^+$ than found in steady state PB suggesting that the two regimens investigated specifically mobilize CD34$^+$BB9$^+$ cells. Analogous observations have previously been made regarding CD90, which is similarly expressed on a significantly higher proportion of CD34$^+$ cells in mobilized blood than in the BM [33].

The epitope identified by BB9 was shown to reside on a 160 kDa cell surface glycoprotein that was not released by PI-PLC nor following treatment with a range of proteases, with the exception of chymopapain. The calculated molecular weight of the BB9 antigen is similar to that of MDR-1, a 170 kDa glycoprotein previously shown to be expressed by primitive human HPC [34]. However, the lack of reactivity of BB9 with peripheral blood leukocytes (PBL) distinguishes it from that of MDR-1, which is expressed by 40-65% of PBL [35]. Moreover, in accord with its vinblastine-resistant phenotype, the T-lymphoid line VLB-100 [36] exhibits high level of expression of MDR-1 but was shown not to bind BB9 at detectable levels. These data therefore suggest that BB9 does not identify MDR-1. Other cell surface glycoproteins with ostensibly similar restricted patterns of expression on primitive human HPC to the antigen identified by BB9 include CD90 [8], AC133 [9,11], Flt3/flk-2 (CD135) [37], Tie-1 [38], KDR [39], TEK [11]. However, these are unlikely to correspond to the BB9 antigen based on several criteria including differences in molecular weight (Thy-1 [7,8], AC133 [40], Tie-1 [43], TEK [41], KDR [42]) and patterns of expression both on primary hematopoietic cells [37,44] and on hematopoietic cell lines [38].

The restricted distribution of the BB9 antigen within hematopoietic tissues, i.e. primitive hematopoietic progenitors and bone marrow stromal cells is intriguing, a pattern of expression also exhibited by several other antigens including CD34 [12,13], CD90 [14], CD164 [15] and Sca-1 [16]. Given the adhesive properties of at least 3 of these glycoproteins [45-48] it is tempting to speculate that BB9 may also function as an adhesion molecule. Initial studies demonstrate that BB9 also binds to vascular endothelial cells in hematopoietic tissues such as spleen, thymus and tonsil, a finding not inconsistent with a proposed adhesive function. However, MAb BB9 does not perturb the adhesion of CD34+ cells to bone marrow stromal cells in vitro (HR, PJS; unpublished observation). Answers to the question of the role of the BB9 antigen in the haemopoietic system will benefit both from further biochemical characterization of the glycoprotein and ultimately from the isolation of a cDNA corresponding to the antigen. Such studies are currently in progress.

TABLE 4 shows expression of BB9 on hematopoietic and other cell lines.

| Cell line | Reactivity | Characteristics of cell line |
| --- | --- | --- |
| UT7 | ++ | Erythroblastic/megakaryocytic leukaemia |
| TF-1 | +/− | Erythroleukaemia |
| K562 | ++ | Erythroblastic leukaemia, Ph+ (CML) |
| MEG-01 | ++ | Megakaryoblastic leukaemia Ph+ (CML) |
| MO7e | − | Megakaryoblastic leukaemia |
| HEL-DR | ++ | Erythroleukaemia |
| Hi MEG | + | Megakaryoblastic leukaemia |
| KG-1 | + | Myeloblastic leukaemia |
| KG-1a | − | Immature subline of KG-1 |
| HL60 | ++ | Myeloblastic leukaemia |
| U937 | + | Histiocytic leukaemia |
| RC2A | + | AML |
| Nalm-6 | + | B cell |
| Hut78 | − | T cell |
| Jurkat | − | T cell |
| Molt-4 | − | T cell |
| CEM VLB-100 | − | T cell |
| Dermal fibroblasts | +++ | Fibroblast |
| MCF-7 | + | Breast carcinoma |
| MG63 | ++ | Osteocarcinoma |

Indirect immunofluorescence was used to assess BB9 expression. Cells were incubated with BB9 MAb at 20 μg/mL for 45 minutes and with PE conjugated goat anti-mouse IgG$_1$ secondary antibody. At least 10,000 events were acquired on a Coulter XL flowcytometer for each cell line examined and the proportion of BB9 positive cells quantitated as follows:

−=0-2%, +/−=2-5%, +=5-35%, ++=35-80%, +++=80-100%.

In summary, we have described a monoclonal antibody, BB9, with specificity for a cell surface glycoprotein co-expressed by bone marrow stromal cells and primitive human HPC within adult BM and mobilized blood. The expression of the BB9 antigen within umbilical cord blood, fetal liver and during embryonic hematopoiesis is currently under investigation. In this respect the possibility that BB9 exhibits binding to CD34$^−$ cells with stem cell activity is of particular interest.

Example 2

Isolated Cells Identified by BB9 Antibody and Transplantation of the Cells

Mononuclear cells were isolated from samples of human umbilical cord blood by density sedimentation on Ficoll-Hypaque (density 1.077 g/ml) according to standard procedures. Prior to immunolabeling, the cord blood mononuclear cells (CBMNC) were incubated in PBS supplemented with human serum albumin (HAS; Baxter Healthcare) and 100 μg/mL aggregated normal human gamma globulin (Sandoglobulin) for 30 minutes on ice to block Fc receptors. Cells were then labelled either with the individual antibodies or simultaneously with a combination of the anti-CD34 MAb 43A1 (mouse IgG$_3$; a generous gift from Dr. H-J. Bühring, University of Tübingen) and antibody BB9 (mouse IgG$_1$) both diluted to a final concentration of 20 μg/mL in PBS-HSA. Additional samples were stained in parallel with isotype-matched, non-binding control IgG$_3$ (Southern Biotechnology Associates, Birmingham, Ala.) or IgG$_1$ (MAb 1B5, anti-Giardia, generously provided by Dr Graham Mayerhofer, Department of Microbiology, University of Adelaide) antibodies either alone or in various pairwise combinations with the 43A1 and BB9 antibodies as appropriate. All antibody incubations were performed for 45 minutes on ice and were followed in all cases by two washes in an excess of PBS-HAS at 4° C. Specifically bound monoclonal antibody was then revealed by incubation with a combination of optimally titred isotype-specific goat antibodies directed against mouse-IgG$_1$ (conjugated to Phycoerythrin, PE) and mouse-IgG$_3$ (conjugated to FITC; both from Southern Biotechnology Associates, Birmingham Ala., USA). After a further two washes in PBS-HAS the cells were suspended at approximately 10$^7$ cells/mL in cold PBS-HSA for FACS.

Cells were sorted into CD34+, CD34+/BB9+ and CD34+/BB9− fractions according to the gates indicated. The sorted cells were transplanted into irradiated NOD/SCID mice (400cGy) at a dose of 50-100,000 cells per mouse together with 10$^7$ irradiated CD34-depleted CBMNC as carrier cells. Engraftment was assessed at week 6 post transplant by flow cytometric analysis of bone marrow and peripheral blood (FIG. 8) from the transplanted NOD/SCID mice with human specific anti-CD45-FITC in pairwise combination with either isotype IgG$_1$-PE, CD11b-PE, CD19-PE or CD34-PE (all reagents from Becton-Dickinson). The results are summarised in Table 5 below.

TABLE 5

Engraftment Results at 6 Week Post-Transplantation

| Population | % Human CD45+ cells (Week 6) |
| --- | --- |
| CD34+ | 15 ± 6.5 |
| CD34+BB9+ | 12 ± 5 |
| CD34+BB9− | 0.25 ± 0.03 |

```
                    SEQUENCE LISTING

<110> The Peter MacCallum Cancer Institute
      Simmons, Paul J
<120> Identification and Isolation of Somatic
      Stem Cells and Uses Thereof
<130> 649197
<160> 2
<170> PatentIn version 3.1
<210> 1
<211> 10
<212> PRT
<213> Artificial sequence
<220>
<221> PEPTIDE
<222> (1) . . . (10)
<223>
<400> 1
Leu Phe Gln Glu Leu Gln Pro Leu Tyr Leu
1               5                   10
<210> 2
<211> 8
<212> PRT
<213> Artificial sequence
<220>
<221> PEPTIDE
<222> (1) . . . (8)
<223>
<400> 2
Glu Ala Asp Asp Phe Phe Thr Ser
1               5
```

Finally, it is to be understood that various other modifications and/or alterations may be made without departing from the spirit of the present invention as outlined herein.

REFERENCES

1. Berenson R J, Bensinger W I, Hill R S, Andrews R G, Garcia-Lopez J, Kalamasz D F, Still B J, Spitzer G, Buckner C D, Bernstein I D, Thomas E D (1991) Engraftment after infusion of CD34+ marrow cells in patients with breast cancer or neuroblastoma. Blood:1717
2. Civin C I, Trischmann T, Fackler M, Bernstein I, Brunning J, Campos L, Greaves M, Kamoun M, Katz D, Lansdorp P, Look A, Seed B, Sutherland D, Tindle R, Uchanska-Ziegler B (1989) Report on the CD34 cluster workshop, in Knapp W, Dorken B, Golk W, Rieber E, Stein H, Schmidt R, von dem Borne A (eds): Leukocyte Typing IV. Oxford, Oxford Press,
3. Krause D S, Fackler M J, Civin C I, May W S (1996): CD34: Structure, Biology and Clinical Utility. Blood 87:1
4. Sutherland H J, Eaves C J, Eaves A C, Dragowska W, Lansdorp P M (1989) Characterization and partial purification of human marrow cells capable of initiating long-term hematopoiesis in vitro. Blood 74:1563
5. Brandt J, Baird N, Lu L, Srour E, Hoffman R (1988) Characterization of a human hematopoietic progenitor cell capable of forming blast cell containing colonies in vitro. J. Clin Invest 82:1017
6. Huang S, Terstappen LWMM (1994) Lymphoid and myeloid differentiation of single human CD34+, HLA-DR+, CD38− hematopoietic stem cells. Blood 83:1515
7. Baum C M, Weissman I L, Tsukamoto A S, Buckle A-M, Peault B (1992) Isolation of a candidate human hematopoietic stem-cell population. P.N.A.S. (U.S.A.) 89:2804
8. Craig W, Kay R, Cutler R L, Lansdorp P M (1993) Expression of Thy-1 on human hematopoietic progenitor cells. J. Exp. Med. 177:1331
9. Yin A H, Miraglia S, Zanjani E D, Almeida-Porada G, Ogawa M, Leary A G, Olweus J, Keamey J, Buck D W. (1997) AC133, a novel marker for human hematopoietic stem and progenitor cells. Blood 15:5002
10. Buhring H J, Seiffert M, Bock T A, Scheding S, Thiel A, Scheffold A, Kanz L, Brugger W (1999) Expression of novel surface antigens on early hematopoietic cells. Ann N Y Acad Sci 872:25
11. de Wynter E A, Buck D, Hart C, Heywood R, Coutinho L H, Clayton A, Rafferty J A, Burt D, Guenechea G, Bueren J A, Gagen D, Fairbairn L J, Lord B I, Testa N G (1998) CD34+AC133+ cells isolated from cord blood are highly enriched in long-term culture-initiating cells, NOD/SCID-repopulating cells and dendritic cell progenitors. Stem Cells 16:387
12. Simmons P J, Torok-Storb B (1991) CD34 expression by stromal precursors in normal human adult bone marrow. Blood 78:2848
13. Waller E K, Olweus J, Lund-Johansen F, Huang S, Nguyen M, Guo G-R, Terstappen L (1995) The "common stem cell" hypothesis reevaluated: Human fetal bone marrow contains separate populations of hematopoietic and stromal progenitors. Blood 85:2422
14. Gronthos S, Simmons P J (1996) The biology and application of human bone marrow stromal cell precursors. J. Hematotherapy 5:15
15. Zannettino A C W, Bühring H-J, Niutta S, Ashman L K, Känz L, Simmons P J (1995) Identification and functional cloning of MGC-24, a mucin-like molecule expressed by haemopoietic progenitors and bone marrow stromal cells: A negative regulator of haemopoiesis. Blood 86:591a (abstract)
16. Satoh M, Mioh H, Shiotsu Y, Ogawa Y, Tamaoki T (1997) Mouse bone marrow stromal cell line MC3T3-G2/PA6 with hematopoietic-supporting activity expresses high levels of stem cell antigen Sca-1. Exp. Hematol. 25:972
17. To L B, Shepperd K M, Haylock D N, Dyson P G, Charles P, Thorp D L, Dale B M, Dart G W, Roberts M M, Sage R E, Juttner C A (1990) Single high doses of cyclophosphamide enable the collection of high numbers of hemopoietic stem cells from the peripheral blood. Exp. Hematol. 18:442
18. Dyson P G, Jackson K A, McClure B J, Rawling T P, To L B (1996) Increased levels of megakaryocyte progenitors in peripheral blood mobilised by chemotherapy and/or haemopoietic growth factor protocols. Bone Marrow Transp. 18:705
19. Gronthos S, Graves S E, Ohta S, Simmons P J (1994) The STRO-1+ fraction of adult human bone marrow contains the osteogenic precursors. Blood 84:4164
20. Halbert C L, Demers G W, Galloway D A (1991) The E7 gene of human papillomavirus type-16 is sufficient for imortalization of human epithelial cells. J. Virol. 65:473
21. Kaur P, Halbert C L (1995) Immortalization of human keratinocytes with human papilloma virus DNA. Methods Cell Sci. 17:117
22. Simmons P J, Gronthos S, Ohta S, Graves S E (1995) Human bone marrow stromal cell precursors: identification and development potential. Bone Marrow Transp. 15 Supp 1:S3
23. Köhler E, Milstein C (1975) Continuous cultures of fused secreting antibody of predefined specificity. Nature 256: 495
24. Goding J W (1980) Antibody production by hybridomas. J. 1 mm. Meth. 39:285
25. Buhring H J, Burkhardt M, Ning Y, Müller C A (1995) Reactivity patterns and epitope mapping of CD34 panel mAbs, in Schlossman S F, Boumsell L, Gilks W, Harlan J M, Kishimoto T, Morimoto C, Ritz J, Shaw S, Silverstein R, Springer T, Tedder TF, Todd RF (eds): Leukocyte Typing V. Oxford, Oxford Press, p 847

26. Baird P N, Simmons P J (1996) Expression of the Wilms' Tumour gene (WT1) in normal hemopoiesis. Exp. Hematol. 25:312
27. O'Connor C G, Ashman L K (1982) Application of the nitrocellulose transfer technique and alkaline phosphatase conjugated anti-immunoglobulin for determination of the specificity of monoclonal antibodies to protein mixtures. J. Imm. Meth. 54:267
28. Miltenyi S, Müller W, Weichel W, Radbruch A (1990) High gradient magnetic cell separation with MACS. Cytometry 11:231
29. Haylock D N, To L B, Dowse T L, Juttner C A, Simmons P J (1992) Ex vivo expansion and maturation of peripheral blood CD34$^+$ cells into the myeloid lineage. Blood 80:1405
30. Marchalonis J J (1969) An enzymatic method for the trace iodination of immunoglobulins and other proteins. Biochem. J. 113:299
31. Gerdes J, Lemke H, Baisch H, Wacker H-H, Schwab U, Stein H (1984) Cell cycle analysis of a cell proliferation-associated human nuclear antigen defined by the monoclonal antibody Ki67. J. Immunol. 133:1710
32. Spangrude G J, Johnson G R (1990) Resting and activated subsets of mouse multipotent hematopoietic stem cells. P.N.A.S. (U.S.A.) 87:7433
33. Murray L, Chen B, Galy A, Chen S, Tushinski R, Uchida N, Negrin R, Tricot G, Jagannath S, Vesole D, Barlogie B, Hoffman R, Tsukamoto A (1995) Enrichment of human hematopoietic stem cell activity in the CD34+Thy-1+Lin-subpopulation from mobilized peripheral blood. Blood 85:368
34. Chaudhary P M, Roninson I B (1991) Expression and activity of P-glycoprotein, a multidrug efflux pump, in human hematopoietic stem cells. Cell 66: 85
35. Chaudhary P M, Mechetner E B, Roninson I B (1992) Expression and activity of the multidrug resistance P-glycoprotein in human peripheral blood lymphocytes. Blood 80:2735
36. Beck W T, Mueller T J, Tanzer L R (1979) Altered surface membrane glycoproteins in vinca alkaloid-resistant human leukemic lymphoblasts. Cancer Res. 39:2070
37. Rappold I, Ziegler B L, Köhler I, Marchetto S, Rosnet 0, Bimbaum D, Simmons P J, Zannettino A C W, Hill B, Neu S, Knapp W, Alitalo R, Alitalo K, Ullrich A, Kanz L, Buhring H-J (1997) Functional and phenotypic characterization of cord blood and bone marrow subsets expressing Flt3 (CD135) receptor tyrosine kinase. Blood 90:111
38. Kukk E, Wartiovaara U, Gunji Y, Kaukonen J, Bühring H-J, Rappold I, Matikainen M-T, Vihko P, Partanen J, Palotie A, Alitalo K, Alitalo R (1997) Analysis of Tie receptor tyrosine kinase in haemopoietic progenitor and leukaemia cells. Br. J. Haematol. 98:195
39. Ziegler B L, Valtieri M, Porada G A, De Maria R, Muller R, Masella B, Gabbianelli M, Casella I, Pelosi E, Bock T, Zanjani E D, Peschle C (1999) KDR receptor: a key marker defining hematopoietic stem cells. Science 285:1553
40. Miraglia S, Godfrey W, Yin A H, Atkins K, Warnke R, Holden J T, Bray R A, Waller E K, Buck D W (1997) A novel five-transmembrane hematopoietic stem cell antigen: isolation, characterization, and molecular cloning. Blood 90:5013
41. Ziegler S F, Bird T A, Schneringer J A, Schooley K A, Baum P R (1993) Molecular cloning and characterization of a novel receptor protein tyrosine kinase from human placenta. Oncogene 8:663
42. Terman B I, Dougher-Vermazen M, Carrion M E, Dimitrov D, Armellino D C, Gospodarowicz D, Bohlen P (1992) Identification of the KDR tyrosine kinase as a receptor for vascular endothelial cell growth factor. Biochem Biophys Res Commun 187:1579
43. Batard P, Sansilvestri P, Scheinecker C, Knapp W, Debili N, Vainchenker W, Bühring H-J, Monier M-N, Kukk E, Partanen J, Matikainen M-T, Alitalo R, Hatzfeld J, Alitalo K (1996) The Tie receptor tyrosine kinase is expressed by human hematopoietic progenitor cells and by a subset of megakaryocytic cells. Blood 87:2212
44. Haylock D N, Horsfall M J, Dowse T L, Ramshaw H S, Niufta S, Protopsaltis S, Peng L, Burrell C, Rappold I, Buhring H-J, Simmons P J (1997) Increased recruitment of hematopoietic progenitor cells underlies the ex vivo expansion potential of FLT3 ligand. Blood 90:2260
45. Healy L, May G, Gale K, Grosveld F, Greaves M, Enver T (1995) The stem cell antigen CD34 functions as a regulator of hemopoietic cell adhesion. P.N.A.S. (U.S.A.) 92:12240
46. He H, Naquet P, Caillol D, Pierres M (1991) Thy-1 supports adhesion of mouse thymocytes to thymic epithelial cells through a Ca2+ independent mechanism. J. Exp. Med. 173:515
47. Zanneftino A C, Buhring H J, Niutta S, Watt S M, Benton M A, Simmons P J (1998) The sialomucin CD164 (MGC-24v) is an adhesive glycoprotein expressed by human hematopoietic progenitors and bone marrow stromal cells that serves as a potent negative regulator of hematopoiesis. Blood 15:2613
48. Doyonnas R, Yi-Hsin Chan J, Butler L H, Rappold I, Lee-Prudhoe J E, Zannettino A C, Simmons P J, Buhring H J, Levesque J P, Watt S M (2000). CD164 monoclonal antibodies that block hemopoietic progenitor cell adhesion and proliferation interact with the first mucin domain of the CD164 receptor. J. Immunol. 15:840

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: synthetic peptide
```

```
-continued

<400> SEQUENCE: 1

Leu Phe Gln Glu Leu Gln Pro Leu Tyr Leu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: synthetic peptide

<400> SEQUENCE: 2

Glu Ala Asp Asp Phe Phe Thr Ser
1               5
```

The invention claimed is:

1. A method of identifying a stem cell comprising the steps of obtaining:
   a cell sample including stem cells;
   detecting the presence of a polypeptide sequence having the sequence LFQELQPLYL (SEQ ID NO:1);
   detecting the presence of at least one stem cell specific marker selected from the group consisting of STRO-1, SH2, SH3, SH4, cytokeratin 14, alpha-6 integrin (CD49F), and c-kit; and
   identifying the stem cells having the sequence of SEQ ID NO:1.

2. A method of identifying a stem cell comprising the steps of:
   obtaining a cell sample including stem cells;
   detecting the presence of a polypeptide sequence having the sequence EADDFFTS (SEQ ID NO:2);
   detecting the presence of at least one stem cell specific marker selected from the group consisting of STRO-1, SH2, SH3, SH4, cytokeratin 14, alpha-6 integrin (CD49F), and c-kit; and
   identifying the stem cells having the sequence of SEQ ID NO:2.

3. A method of identifying a stem cell comprising the steps of:
   obtaining a cell sample including stem cells;
   detecting the presence of angiotensin converting enzyme (ACE) on a cell;
   detecting the presence of at least one stem cell specific marker selected from the group consisting of STRO-1, SH2, SH3, SH4, cytokeratin 14, alpha-6 integrin (CD49F), and c-kit; and
   identifying the stem cells having ACE.

4. A method according to claim 3 wherein ACE is detected by the presence of a polypeptide comprising the amino acid sequence of SEQ ID NO:1, SEQ ID NO:2 or both SEQ ID NO:1 and SEQ ID NO:2.

5. A method according to any one of claims 1 to 4 wherein the stem cell is a somatic stem cell.

6. A method according to claim 5 wherein the somatic stem cell is selected from the group consisting of haematopoietic stem cells, mesenchymal stem cells, keratinocyte stem cells, neuronal stem cells, hepatic stem cells and pancreatic stem cells.

7. A method according to claim 6 wherein the stem cell is a haematopoietic stem cell.

8. A method according to any one of claims 1 to 4 wherein the cell sample including stem cells is obtained from a stem cell source selected from the group consisting of the bone marrow; blood; embryonic yolk sac; fetal liver; spleen; skin; dermis; liver; brain; pancreas and kidney.

9. A method according to any of claims 1 to 4 wherein the detection comprises the use of a means selected from the group consisting of antibodies to ACE or a polypeptide comprising the amino acid sequence of SEQ ID NO:1, SEQ ID NO:2, or both SEQ ID NO:1 and SEQ ID NO:2; agonists and antagonists against ACE or the amino acid sequences of SEQ ID NO:1 or SEQ ID NO:2; nucleic acid detection systems which can detect expression of ACE or the amino acid sequences of SEQ ID NO:1 or SEQ ID NO:2 either by the presence of DNA, RNA, mRNA or ACE protein; and enzymatic, fluorescence or colourimetric assays for ACE or the amino acid sequence of SEQ ID NO:1 or SEQ ID NO:2.

10. A method according to claim 9 wherein the detection of ACE is performed using an antibody to ACE or a polypeptide comprising the amino acid sequence of SEQ ID NO:1, SEQ ID NO:2 or both SEQ ID NO:1 or SEQ ID NO:2.

11. A method according to claim 10 wherein the antibody is antibody BB9.

12. A method for obtaining a cell population enriched in stem cells comprising the steps of:
   obtaining a cell population comprising stem cells;
   detecting the presence of angiotensin converting enzyme (ACE) on a cell; and
   selecting for cells that are identified by the presence of ACE or a fragment and at least one stem cell specific marker selected from the group consisting of STRO-1, SH2, SH3, SH4, cytokeratin 14, alpha-6 integrin (CD49F), and c-kit on the cell.

13. A method according to claim 12 wherein ACE is detected by the presence of a polypeptide comprising the amino acid sequence of SEQ ID NO:1, SEQ ID NO:2 or both SEQ ID NO:1 and SEQ ID NO:2.

14. A method according to claim 12 or 13 wherein the presence of ACE is detected by an antibody for ACE.

15. A method according to claim 14 wherein the antibody is BB9.

16. A method according claim 12 or claim 13 wherein the stem cells are haematopoietic stem cells.

17. A method of removing stem cells from a population comprising the steps of:
obtaining a cell population comprising stem cells;
detecting the presence of angiotensin converting enzyme (ACE) on a cell; and
selecting out those cells which are identified by the presence of ACE and at least one stem cell specific marker selected from the group consisting of STRO-1, SH2, SH3, SH4, cytokeratin 14, alpha-6 integrin (CD49F), and c-kit on the cell.

18. A method according to claim 17 wherein ACE is detected by the presence of a polypeptide comprising the amino acid sequence of SEQ ID NO:1, SEQ ID NO:2 or both SEQ ID NO:1 and SEQ ID NO:2.

19. A method according to claim 17 or 18 wherein the presence of ACE is detected by an antibody for ACE.

20. A method according to claim 19 wherein the antibody is BB9.

21. A method of isolating a stem cell comprising obtaining a cell population comprising stem cells;
detecting the presence of angiotensin converting enzyme (ACE) on a cell;
selecting for those cells which are identified by the presence of ACE and at least one stem cell specific marker selected from the group consisting of STRO-1, SH2, SH3, SH4, cytokeratin 14, alpha-6 integrin (CD49F), and c-kit on the cell; and
isolating those cells identified by the presence of ACE and at least one stem cell specific marker selected from the group consisting of STRO-1, SH2, SH3, SH4, cytokeratin 14, alpha-6 integrin (CD49F), and c-kit.

22. A method according to claim 21 wherein ACE is detected by the presence of a polypeptide comprising the amino acid sequence of SEQ ID NO:1, SEQ ID NO:2 or both SEQ ID NO:1 and SEQ ID NO:2.

23. A method according to claim 21 or 22 wherein the presence of ACE is detected by an antibody for ACE.

24. A method according to claim 23 wherein the antibody is BB9.

25. A method according to claim 21 or claim 22 wherein the stem cell is a haematopoietic stem cell.

* * * * *

UNITED STATES PATENT AND TRADEMARK OFFICE
CERTIFICATE OF CORRECTION

| | | |
|---|---|---|
| PATENT NO. | : 7,718,376 B2 | Page 1 of 1 |
| APPLICATION NO. | : 10/486845 | |
| DATED | : May 18, 2010 | |
| INVENTOR(S) | : Simmons | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 758 days.

Signed and Sealed this
Eleventh Day of January, 2011

David J. Kappos
*Director of the United States Patent and Trademark Office*